US007888321B2

(12) United States Patent
Cooper et al.

(10) Patent No.: US 7,888,321 B2
(45) Date of Patent: Feb. 15, 2011

(54) PRODUCTION OF HIGH LEVELS OF TRANSGENIC FACTOR IX WITHOUT GENE RESCUE, AND ITS THERAPEUTIC USES

(75) Inventors: Julian D. Cooper, Blacksburg, VA (US); William Hugold Velander, Blacksburg, VA (US); Tanya K. O'Sickey, Terre Haute, IN (US)

(73) Assignee: Progenetics LLC, Blacksburg, VA (US)

( * ) Notice: Subject to any disclaimer, the term of this patent is extended or adjusted under 35 U.S.C. 154(b) by 0 days.

(21) Appl. No.: 12/255,325

(22) Filed: Oct. 21, 2008

(65) Prior Publication Data

US 2009/0239797 A1 Sep. 24, 2009

Related U.S. Application Data

(63) Continuation of application No. 10/471,492, filed as application No. PCT/US02/07532 on Mar. 11, 2002, now abandoned.

(60) Provisional application No. 60/274,983, filed on Mar. 12, 2001.

(51) Int. Cl.
A61K 35/14 (2006.01)
A61K 38/00 (2006.01)
C12P 21/00 (2006.01)
A01K 67/027 (2006.01)

(52) U.S. Cl. .............................. 514/12; 530/383; 800/7; 800/17

(58) Field of Classification Search ........................ None
See application file for complete search history.

(56) References Cited

U.S. PATENT DOCUMENTS

| 4,348,384 | A | 9/1982 | Horikoshi et al. |
| 4,786,726 | A | 11/1988 | Smith |
| 4,873,316 | A | 10/1989 | Meade et al. |
| 5,171,569 | A | 12/1992 | Anson et al. |
| 5,322,775 | A | 6/1994 | Clark et al. |
| 5,366,894 | A | 11/1994 | Clark et al. |
| 5,476,995 | A | 12/1995 | Clark et al. |
| 5,589,604 | A | 12/1996 | Drohan et al. |
| 5,831,141 | A | 11/1998 | Lubon et al. |
| 5,948,407 | A | 9/1999 | McGuinness et al. |
| 6,046,380 | A | 4/2000 | Clark et al. |
| 6,344,596 | B1 | 2/2002 | Velander et al. |
| 7,220,718 | B2 | 5/2007 | Alpan et al. |
| 7,419,948 | B2 | 9/2008 | Velander et al. |
| 2002/0166130 | A1 | 11/2002 | Velander et al. |
| 2004/0133930 | A1 | 7/2004 | Cooper et al. |

FOREIGN PATENT DOCUMENTS

| EP | 0 451 823 A2 | 10/1991 |
| EP | 0 791 652 A1 | 8/1997 |
| EP | 0 274 489 B1 | 10/1997 |
| EP | 0 396 699 B1 | 10/1997 |
| GB | 2 125 409 A | 3/1984 |
| WO | WO 90/05188 A1 | 5/1990 |
| WO | WO 91/08216 A1 | 6/1991 |
| WO | WO 94/05796 A1 | 3/1994 |
| WO | WO 95/30000 A1 | 11/1995 |
| WO | WO 98/35689 A1 | 8/1998 |

OTHER PUBLICATIONS

Aguirre et al., "Expression of human erythroporetin transgenes and of the endogenous wap gene in the mammary gland of transgenic rabbits during gestation and lactation," *Transgenic Research* 7:311-317 (1998).

Anson et al., "Expression of active human clotting factor IX from recombinant DNA clones in mammalian cells," *Nature* 315:683-685 (1985).

Clark et al., "Expression of Human Anti-Hemophilic Factor IX in the Milk of Transgenic Sheep," *Bio/Technology* 7:487-492 (1989).

Drohan et al., "Inefficient processing of human protein C in the mouse mammary gland," *Transgenic Res.* 3:355-364 (1994).

Hemker et al., "Oral treatment of hemophilia A by gastrointestinal absorption of factor VIII entrapped in liposomes," *Lancet I*: 70-71 (1980).

Kim et al., "Purified Factor IX Using Monoclonal Immunoaffinity Technique: Clinical Trials in Hemophilia B and Comparison to Prothrombin Complex Concentrates," *Blood* 79(3):568-575 (1992).

Massoud et al., "The deleterious effects of human erythropoietin gene driven by the rabbit whey acidic protein gene promoter in transgenic rabbits," *Reprod. Nutr. Dev.* 36:555-563 (1996).

Morcol et al., "The Porcine Mammary Gland as a Bioreactor for Complex Proteins," *Ann. N.Y. Acad Sci.* 721:218-233 (1994).

Velander et al., "High-level expression of a heterologous protein in the milk of transgenic swine using the cDNA encoding human protein C," *Proc. Natl. Acad. Sci. USA* 89:12003-12007 (1992).

Wall, "Transgenic Livestock: Progress and Prospects for the Future," *Theriogenology* 45:57-68 (1996).

(Continued)

*Primary Examiner*—Deborah Crouch
(74) *Attorney, Agent, or Firm*—Cooley LLP

(57) ABSTRACT

A non-human transgenic mammalian animal, as described above, contains an exogenous double stranded DNA sequence stably integrated into the genome of the animal, which comprises cis-acting regulatory units operably linked to a DNA sequence encoding human FIX protein without the benefit of the presence of a complete milk gene sequence for gene rescue, and a signal sequence is active in directing newly expressed Factor IX into the milk of the animal at levels in an unactivated form that is suitable for subsequent processing for therapeutic applications in treating Hemophilia B. The transgenic mammals are preferably pigs, cows, sheep, goats and rabbits. The applications include milk derivatives for oral delivery and oral tolerization in the treatment of Hemophilia B.

20 Claims, 4 Drawing Sheets

OTHER PUBLICATIONS

Wright et al., "High Level Expression of Active Human Alpha-1-Antitrypsin in the Milk of Transgenic Sheep," *Bio/Technology* 9:830-834 (1991).

Yull et al., "Fixing human factor IX (fIX): Correction of a cryptic RNA splice enables the production of biologically active fIX in the mammary gland of transgenic mice," *Proc. Natl. Acad. Sci. USA* 92:10899-10903 (1995).

Sabatino et al., "Generation of Whey Acidic Protein Promoter-Human Factor IX Transgenic Mice for Studies of Oral Tolerance to Human Factor IX in Neonatal Hemophilia B Mice," Hemophilia and Von Willebrand Disease 98:825a-826a (2001).

Furie et al., "A Practical Guide to the Evaluation and Treatment of Hemophilia," Blood 84:3-9 (1994).

Lee, "Reombinant Clotting Factors in the Treatment of Hemophilia," Thrombosis Haemostasis 82:516-524 (1999).

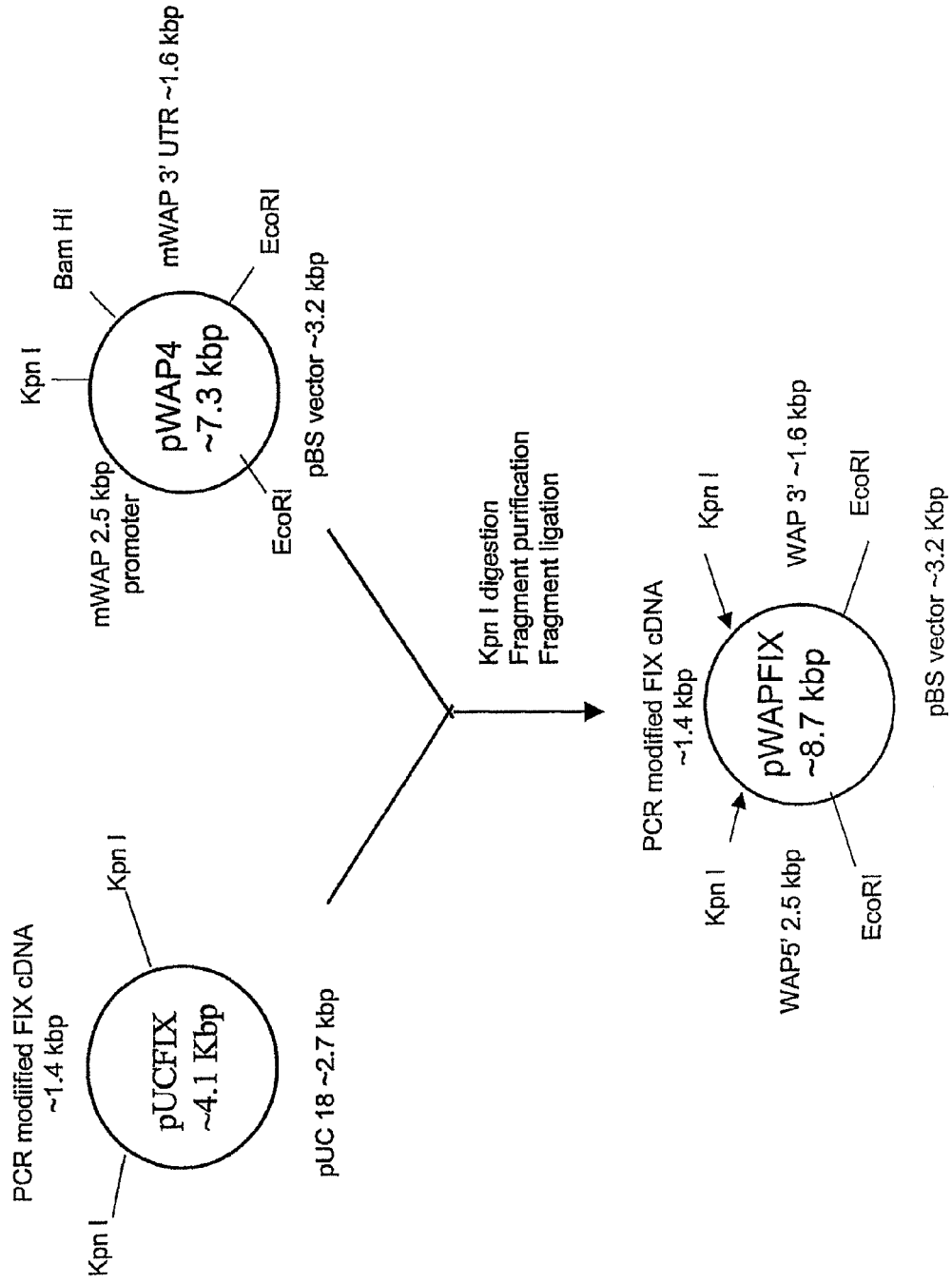
Figure 1. Assembly of the plasmid pWAPFIX

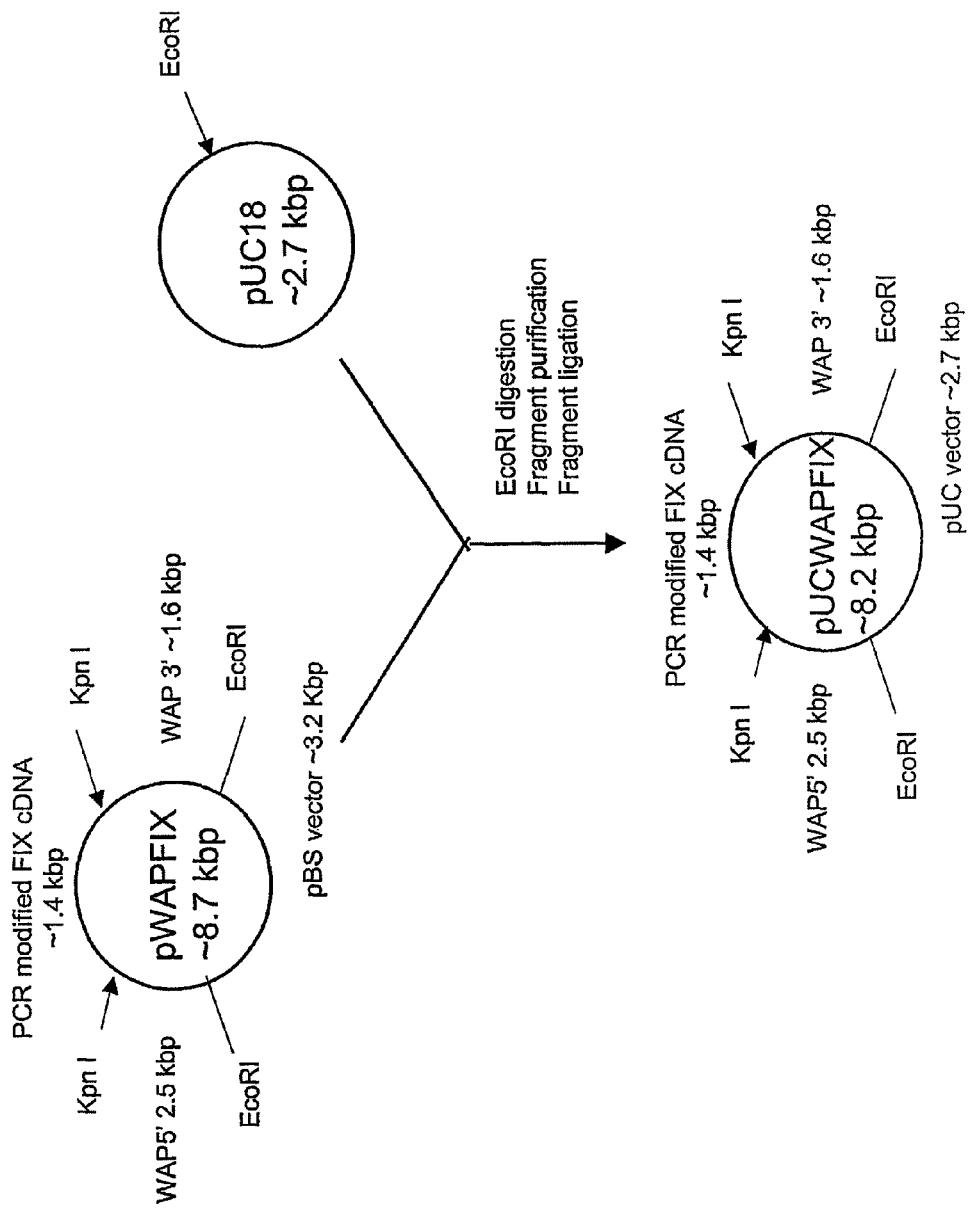
Figure 2. Assembly of the plasmid pUCWAPFIX

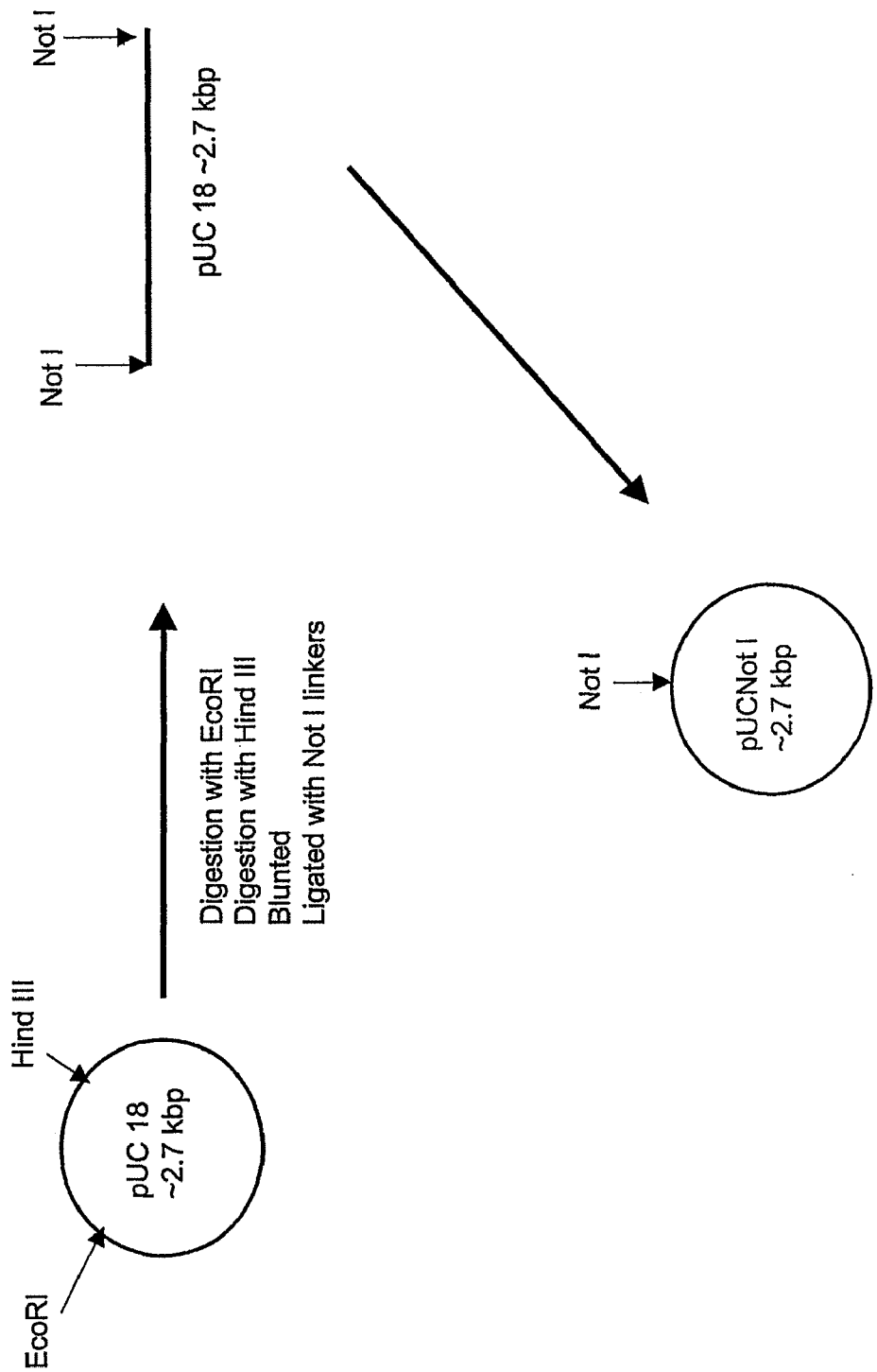
Figure 3. Production of the modified plasmid pUCNot I

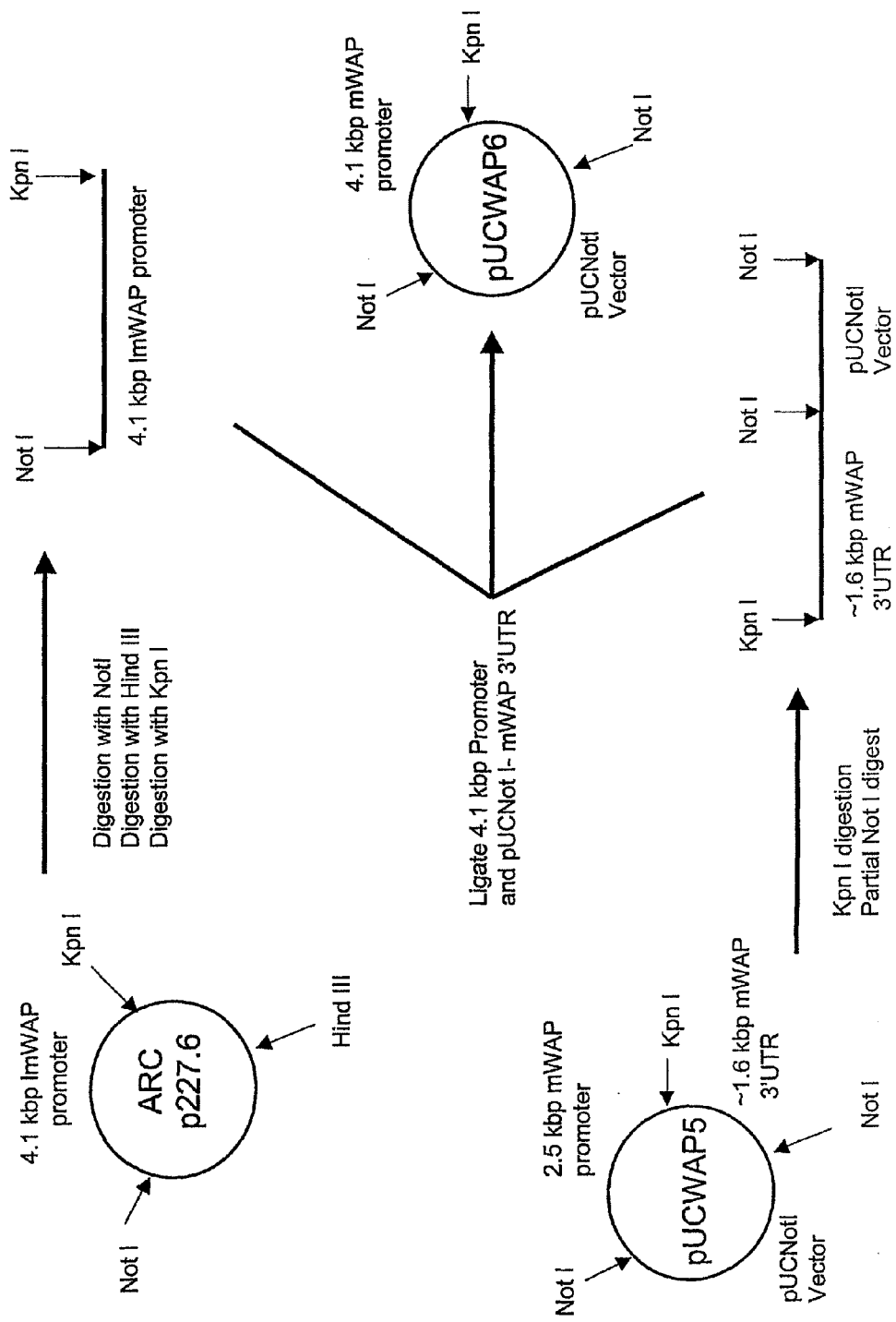
Figure 4. Production of pUCWAP6

PRODUCTION OF HIGH LEVELS OF TRANSGENIC FACTOR IX WITHOUT GENE RESCUE, AND ITS THERAPEUTIC USES

This application is a continuation under 37 C.F.R. §1.53(b) of patent application Ser. No. 10/471,492 filed on Feb. 12, 2004, now abandoned which is a 371 of PCT/US02/07532, filed Mar. 11, 2002, which claims benefit of U.S. Provisional Application No. 60/274,983 filed Mar. 12, 2001, each of which are incorporated herein by reference in their entirety.

FIELD OF THE INVENTION

The invention provides, among other things, a system for producing transgenic proteins, compositions comprising transgenic proteins, transgenic organisms for making proteins, for modifying transgenic proteins in vivo. Illustrative embodiments of the invention particularly provide transgenic animals that express an exogenous gene for vitamin K-dependent proteins, protease inhibitors, blood clotting proteins and mammalian relaxins. In a highly particular illustrative embodiment in this regard the invention provides transgenic female pigs that express these same proteins in their milk in a temporally controlled manner during lactation using a multi-gene inducible system. In this regard, the invention relates particularly to female pigs having stably incorporated in their genomes non-endogenous DNA comprising a region that encodes these same proteins operably linked to a multi-gene system containing at least two different promoters in separate DNA constructs, where one of these promoters is a non-mammary gland specific promoter. Further in this regard the invention relates to the mill containing these same proteins and corresponding compositions derived from the milk. And it also relates to, among other things, uses of these proteins in wellness and therapeutic applications.

BACKGROUND

The concept of producing important pharmaceutical and nutriceutical proteins in transgenic animals is now firmly established (Van Cott, K. E. and Velander, W. H., Exp. Opin. Invest. Drugs, 7(10): 1683-1690 (1998)), with three potential products, alpha-1 antitrypsin, antithrombin III and alpha glucosidase in the late stages of clinical trials. These proteins, and nearly all other transgenic polypeptides being developed commercially, were produced from a single DNA construct designed to produce a single polypeptide. In general terms, this "classical" design incorporates three distinct regions of DNA, which are all joined or operably linked in one contiguous strand.

The first region of DNA is a tissue specific promoter, in the above mentioned examples a milk protein promoter, which directs expression of the gene to a target organ, the mammary gland, which is regulated by lactogenic hormones, growth factors, cell-cell and cell-substratum interactions. The second region of DNA is the coding region, which may consist of complimentary DNA (cDNA, containing no introns), genomic DNA (gDNA) or a combination of both in a format called a mini-gene. It is important to note that cDNAs, and perhaps also minigenes, have a silencing effect (failure to express or poor expression levels) on adjacent transgenes (Clark, A. J., et al., NAR, 25 (5), 1009-1014, 1997). Therefore, a method of overcoming this silencing effect using non-genomic DNA sequences is highly desirable. The coding region contains the information needed to produce a specific protein, including any processing and secretory signals. The third region, the 3' region, contains further regulatory sequences and may influence the quantity of polypeptide that is produced from that construct. Non-genomic DNA sequences are inherently smaller than gDNA sequences and are therefore, much easier to manipulate in classical transgene formats.

Although this classical design has been successful in producing commercially viable quantities of certain proteins, there are two areas in which this system is not optimal. First, it is generally accepted that using cDNAs or minigenes in a classically designed construct, is less efficient for protein production than using a corresponding gDNA coding region. Indeed, this is such a problem that methods have been developed to address this issue (Clark, A. J. et al, Biotechnology 10, 1450-1454, 1992). Whilst these methods can improve the efficiency and level of expression of cDNAs and minigenes to some extent, they do not improve expression to the same level as is typically obtained using gDNA. A higher level would be ideal for commercial protein production.

The second area in which the classical single gene DNA construct design is suboptimal is in the production of highly biologically active proteins in transgenic animals. Proteins with an extremely high biological activity can be detrimental to the transgenic animal, even if circulatory levels (or other systemic levels) are low (Castro, F. O., et al., Selection of Genes for Expression in Milk: The Case of the Human EPO Gene, in Mammary Gland Transgenesis. Therapeutic Protein Production. Castro and Janne (eds.) Springer-Verlag Berlin N.Y., 91-106, 1998). This can be due in large part to either ectopic expression (expression of the transgene in organs other than the targeted one) or leakage of the protein product into the blood from the target organ. If the protein product is highly biologically active, expression ideally must be strictly controlled so that the animal is exposed to the product for a short time only, thus reducing the chance of any lasting detrimental effects. This requires an expression system that can be turned on and off very rapidly and precisely.

Regulation of Promoters

The expression of many genes is controlled at the level of transcription, when the DNA sequences are transcribed into RNA, prior to being translated into protein (Latchman, D. S., Eukaryotic Transcription Factors, Academic Press, 1998). The DNA sequence element that controls transcription is the promoter. This generally contains a small core region, which is capable of directing constitutive or basal levels of transcription, and upstream response elements that control spatial and temporal regulation of transcription. These DNA sequences include two types of elements, those which are involved in the basic process of transcription and are found in many genes exhibiting distinct patterns of regulation, and those found only in genes transcribed in a particular tissue or in response to a specific signal. The latter elements likely produce this specific expression pattern. They are binding sites for a wide range of different cellular proteins (transcription factors) whose levels fluctuate in response to stimuli from external or internal sources, Gene expression in a given tissue may be stimulated or inhibited depending on the type and amount of transcription factors that are present in that tissue at any time. Many transcription factors or other proteins that enable transcription factor pathways are largely uncharacterized from the perspective of an exact biochemical analysis, which details their conformationally-dependent interactions with DNA. Overall, the regulation of expression at the DNA level, is a function of which regulatory elements (binding sites) are present in the promoter and how the cell or tissue responds to its environment by changing the relative levels of the different DNA binding transcription factors in the cell.

Another mechanism involved in the precise control of gene expression is transcriptional repression (Maldonado, E., et al, Cell, 99(5), 455-458, 1999). Transcriptional repressor proteins associate with their target genes either directly through a DNA-binding domain or indirectly by interacting with other DNA-bound proteins. The repressor protein can inhibit transcription by masking a transcriptional activation domain, blocking the interaction of an activator with other transcription components or by displacing an activator from the DNA.

Milk protein genes are characterized by a strict tissue specific expression and regulation during the process of functional differentiation. They are coordinately expressed in response to various developmental signals, such as changing levels of lactogenic hormones (prolactin, insulin, glucocorticoids, progesterone), local levels of certain growth factors (EGF), cell-cell interactions and interactions with extra-cellular matrix (ECM) components (Rijnkels, M. and Pieper, F. R., Casein Gene-Based Mammary Gland-Specific Transgene Expression, in Mammary Gland Transgenesis. Therapeutic Protein Production. Castro and Janne (eds.) Springer-Verlag, Berlin, N.Y., 41-64, 1998).

Lactogenic hormones activate latent transcription factors in the cytoplasm of mammary epithelial cells. The steroid hormones progesterone, estrogen, and glucocorticoid regulate the transcription of target genes by binding to specific intracellular receptors. Some models purport that binding of the hormone with its receptor changes the receptor's conformation from a physiologically inactive form to a form which is active and capable of dimerization. The active receptors are then capable of binding specific DNA sites in the regulatory region of the target gene promoters, stimulating gene transcription and thus, protein synthesis. Steroid receptors belong to a superfamily of ligand-inducible transcription factors and it has been well documented that these are modular proteins organized into structurally and functionally defined domains. It has also been shown that these domains can be rearranged as independent cassettes within their own molecules or as hybrid molecules with domains from other regulatory peptides. Interestingly, the transactivation domains of the glucocorticoid receptor can be duplicated in tandem and show positional independence in a "super receptor" with 3-4 times the activity of the wild type protein. (Hollenberg, S. M. and Evans, R. M., Cell, 55, 899-906, 1988; Fuller, P. J., FASEB J., 5, 3092-3099, 1991; U.S. Pat. No. 5,364,791; U.S. Pat. No. 5,935,934; Whitfield, G. K., et al, J. Cell. Biochem., suppl. 32-33, 110-122, 1999; Braselmann, S., et al, PNAS, 90, 1657-1666, 1993). The structure and function of the steroid receptor superfamily is well conserved. Generally there are three main domains and several sub-domains or regions. The NH2-terminal domain is the least conserved in size and sequence and contains one of the two, transactivation sequences of the receptor. The central DNA binding domain of about 70 amino acids is highly conserved, as is the COOH-terminal ligand binding domain. This latter domain also contains sub-domains responsible for dimerization, heat shock protein (lisp) 90 binding, nuclear localization and transactivation.

Prolactin plays the essential role in milk protein gene expression and exerts its effect through binding to the extracellular domain of the prolactin receptor and through receptor dimerization. This activates a protein tyrosine kinase (JAK2) which is non-covalently associated with the cytoplasmic domain of the prolactin receptor (Gouilleux, F., et al, EMBO J., 13(18), 4361-4369, 1994; Imada, K. and Leonard, W. J., Mol. Immunol., 37 (1-2), 1-11, 2000). The activated JAK2 phosphorylates the signal transducer and transcription activator, Stat 5, causing it to dimerize and subsequently, translocate to the nucleus. Once in the nucleus, Stat5 specifically binds to sequence elements in the promoter regions of milk protein genes (Liu, X., et al, PNAS, 92, 8831-8835, 1995; Cella, N., et al, Mol. Cell. Biol., 18(4), 1783-1792, 1998; Mayr, S., et al, Eur. J. Biochem., 258(2), 784-793, 1998). In an analysis of 28 milk protein gene promoters (Malewski, T., BioSystems, 45, 29-44, 1998) there were 4 transcription factor binding sites that were present in every promoter, C/EBP, CTF/NF1 MAF and MGF (Stat 5). Although steroid hormone receptors and Stat factors comprise two distinct families of inducible transcription factors their basic structure is similar. Stat proteins are modular with an amino terminus that regulates nuclear translocation and mediates the interaction between Stat dimers (Callus, B. A. and Mathey-Prevot, B., J. Biol. Chem., 275(22), 16954-16962, 2000). There is a central DNA binding domain and a carboxy terminal region, which contains the phosphorylation site and a transactivation domain.

Egg white genes seem to be regulated in a similarly complex manner. It is known that the progesterone-dependent activation of the egg white genes in the chicken oviduct is mediated through the progesterone receptor (Dobson, A. D. W., et al, J. Biol. Chem., 264(7), 4207-4211, 1989). In addition, the chicken ovalbumin upstream promoter-transcription factor (COUP-TF) is a high affinity and specific DNA binding protein, which interacts as a dimer with the distal promoter sequence of the ovalbumin gene and promotes initiation of transcription of this gene by RNA polymerase (O'Malley, B. W. and Tsai, M-J., Biol. Reprod., 46, 163-167, 1992). COUP-TFs are orphan members (no binding ligand has as yet been determined for these receptors) of the nuclear receptor superfamily, and have been shown to play a key role in the regulation of organogenesis, neurogenesis, metabolic enzyme production and cellular differentiation during embryogenic development, via transcriptional repression and activation (Sugiyama, T., et al, J. Biol. Chem., 275(5), 3446-3454, 2000).

A protein expression method based on the inducible Tet repressor system has been developed (Furth, P. A., et al, PNAS, 91, 9302-9306, 1994), but the levels of basal expression without induction are too high to be useful in transgenic animals (Soulier S. et al, Eur. J. Biochem. 260, 533-539, 1999). Another inducible system based on the use of the ecdysone receptor has been reported (No, D., et al, PNAS, 93, 3346-3351, 1996; PCT 97/38117, PCT 99/58155) and has recently given encouraging results in transgenic mice (Albanese, C., et al, FASEB J., 14, 877-884, 2000). However, this system required the delivery of an exogenous ligand to the mice for the full lactation period. Such a ligand would be costly and difficult to procure for regular administration in a production environment.

A new multi-gene system for protein production in transgenic animals would improve commercial levels of production from cDNA constructs by amplifying specifically tailored transcription factors which need not naturally occur in the tissue targeted for expression, but would be transgenically expressed specifically in that tissue. Unlike classical gene expression formats for recombinant proteins, the tissue specific promoter would not be linked to the protein to be expressed, but would be used to drive expression of transcription factors which do not have a signal sequence and so are not secreted. In addition, the added control that a doubly inducible multi-gene system would provide, which is inexpensive and easily applied, could enable the production of highly biologically active proteins in transgenic animals in a pulsatile fashion so as to avoid longterm detrimental effects.

Proteins for Transgenic Production

A multi-gene system, as described below, can be used to direct expression of any protein, particularly any secreted protein, which can be expressed in a transgenic organism in useful quantities, either for research or commercial development. Particular proteins of interest with respect to production by multi-gene expression systems include relaxin and other hormones with cross-species activity such as growth factors, erythropoitin (EPO) and other blood cell growth stimulating factors. For these proteins, the expression may be problematic in terms of harming the host animal as is known to happen when EPO is expressed for an extended period of time. It is noted that tissue specific expression of transgenes is not an absolute phenomenon and promiscuous expression or systemic transport of the expressed recombinant protein within the animal almost always occurs with any expression system in any animal, albeit at very low levels. However, even at low levels of expression of EPO, when the EPO is expressed over an extended period of time, the hematocrit of the host animal can rise to a fatal level. Thus a temporal control which can enable pulse expression using an external inducer molecule could overcome the problems of continuous and extended expression (ie., as could occur if expression occurs over an entire lactation period). Pulse or truncated expression would be useful in preventing an adverse, systemic physiologic effect by recombinant molecules like EPO, which can cause these effects at very low levels.

Relaxin is widely known as a hormone of pregnancy and parturition and typically circulates at less than 50 pg/ml in the blood of women. However, it is now emerging that the peptide has a far wider biological function than was at first thought. There are receptor sites for relaxin in striated muscle, smooth muscle, cardiac muscle, connective tissue, the autonomic and the central nervous systems. Human relaxin has been demonstrated to inhibit excessive connective tissue build-up and is in Phase II trials for the treatment of Scleroderma. Porcine relaxin was available commercially in the 1950-60s and was used extensively for such conditions as cervical ripening, scleroderma, premature labour, PMS, decubital ulcers and glaucoma. Relaxin is known to adversely affect the lactation of different mammalian species but does not seem to affect the pig in a similar manner. Therefore, the pig is perfectly suited for production of relaxin in milk.

Other examples of proteins which it would be desirable to produce in transgenic organisms, are proteins that are protease inhibitors. Some examples of protease inhibitors are Alpha 1-antitrypsin, Alpha 2 Macroglobulin, and serum leukocyte protease inhibitor. These proteins are serine protease inhibitors that show antiviral, non-steroidal anti-inflammatory and wound healing properties. These proteins are useful in veterinary, cosmetic and nutriceutical applications.

Alpha 1-antitrypsin (AAT) is a naturally occurring glycoprotein produced by the liver. Improperly glycosylated recombinant AAT such as made by yeast, does not have a sufficient circulation half-life to be used as a parenterally administered therapeutic. Congenital deficiency results in the condition emphysema and in 1985 Bayer Pharmaceuticals began marketing a plasma derived AAT product, Prolastin. Unfortunately, due to shortages of Asafe@ plasma and frequent recalls, supplies of Prolastin are often very limited. AAT has also been used to treat psoriasis, atopic dermatitis, ear inflammation, cystic fibrosis and emphysema, and to assist in wound healing. It has been estimated that over 10 million people in the US alone may benefit from AAT therapies.

Alpha 2 macroglobulin (A2M) is a very large, complex glycoprotein with a published cDNA sequence containing 1451 amino acids. The mature protein is a tetrameric molecule composed of four 180 kDa subunits and thus has a molecular weight which is over 720 kDa. Its complexity makes it most suited for production in mammalian systems but few mammalian systems will likely make A2M at commercially viable levels. A2M is indicated for treatment of asthma, bronchial inflammation and eczema and acts as a protease inhibitor to both endogenous and exogenous proteases that cause inflammation. A2M is necessarily more potent than alpha 1-antitrypsin due to its irreversible binding of target proteases. A2M is also useful in inhibiting proteases frequently found in (thermal) burn wounds from yeast and other infections. The high specific activity of these types of proteases allows for smaller doses during treatment. Thus, A2M=s complexity and specific activity make it ideally suited for production in transgenic pig mammary glands.

Vitamin K-Dependent Proteins

Vitamin K-dependent (VKD) proteins such as those proteins associated with haemostasis have complex functions which are largely directed by their primary amino acid structure. In particular, the post-translational modification of glutamic acids in the amino terminal portion of these molecules is essential for proper biological activity. This includes biological activity of both pro-coagulation and anti-coagulation. This particular domain found in VKD-proteins is called the "gla domain". For example, the Gla domain is an essential recognition sequence in tissue factor (TF) mediated pro-coagulation pathways. The anti-coagulation of this pathway depends upon the lipoprotein-associated coagulation inhibitor, termed LACI, which is a non-VKD protein. LACI forms a complex with the Gla domain of factor Xa, factor VIIa, and TF. Specifically, the Gla domain of factor Xa (FXa) is needed for this procoagulation inhibitory activity. It has been shown that recombinant chimeric molecules having LACI inhibitor (Kunitz type) regions and the Gla domain of FXa can be inhibitory of the TF pathway.

TABLE 1

| VKD proteins. | | |
|---|---|---|
| Protein C | Factor X(FX) | Bone Gla protein (Osteocalcin) |
| Protein S | Prothrombin | |
| Protein Z | Factor VII | |
| Factor IX | | |

Gamma-carboxylation is required for calcium-dependent membrane binding. All of the proteins listed in Table 1 have multiple Gla-residues in a concentrated domain. The Gla-domains of these proteins mediate interaction and the formation of multi-protein coagulation protein complexes. Mammalian coagulation (here collectively meaning both pro-coagulation and anti-coagulation pathways and mechanisms) physiology requires that nearly complete-carboxylation of VKD-proteins occurs within the respective Gla domain for each of these proteins to be maximally functional. Notably, in the context of recombinant synthesis of any protein containing Gla-domains, the extent of gamma-carboxylation of VKD-proteins varies from one mammalian cell source to another, including differences between species and tissue within a species.

VKD-proteins of interest with respect to production by single or multi gene expression systems include those in Table 1, particularly blood clotting factor IX, Protein C and chimeric hybrid vitamin K-dependent proteins. Factor IX is an essential blood clotting protein. Haemophilia B is a genetic disorder in which the production of active Factor IX is defective. It is an inherited disorder that primarily affects males, at the rate of approximately 1 in 30,000. The consequent inability to produce sufficient active Factor IX can lead to profuse bleeding, both internally and externally, either spontaneously or from relatively minor injuries.

In spite of techniques available to amplify recombinant synthesis of VKD proteins such as Protein C and Factor IX, biologically functional recombinant versions of these proteins are difficult to produce and are made typically at levels less than about 0.1 grams per liter per 24 hours in recombinant cell culture media (Grinnell, B. W., et al, in Protein C and Related Anticoagulants. Bruley, D. F. and Drohan, W. N. (eds.), Houston, Tex.; Gulf Publishing Company, 29-63, 1990), or less than 0.22 gm per liter per hour in the milk of transgenic livestock (Van Cott, K. E., et al., Genetic Analysis: Biomolecular Eng., 15, 155-160, 1999). The expression of high levels of FIX using a cDNA construct is difficult. However, the gDNA of FIX, at 33 kbp, is rather large and difficult to manipulate, particularly when compared to the FIX cDNA, which is only 1.4 kbp.

Most VKD-blood plasma proteins are also glycosylated. The extent and types of glycosylation observed is heterogeneous and varies considerably in all species and cell types within a species. Examples of the heterogeneity, structure function relationships of glycosylation are cited by Degen, Seminars in Thrombosis and Hemostasis, 18(2), 230-242, 1992; Prothrombin and Other Vitamin K Proteins, Vols I and II, Seegers and Walz, Eds., CRC Press, Boca Raton, Fla., 1986.

Glycosylation is a complex post translational modification that occurs on many therapeutic proteins. The process of glycosylation attaches polymeric sugar compounds to the backbone of a protein. These sugar-based structures impart not only an immunologically specific signature upon the protein, but also can change the specific level of activity that the protein has with relation to how long it can reside in the bloodstream of a patient, or how active the protein is in its basic function. All three of these facets can make or break the protein in its role as a therapeutic or wellness product. For example, genetically engineered yeast can impart glycosylation that results in an immunologically adverse signature, which can stimulate the body to make antibodies and essentially reject the protein. In fact, that is part of the reason why yeast vaccines are effective; they easily induce an immune response. The mammary gland of ruminants produces a substantial fraction of glycosylation on milk proteins which resemble the primitive sugars found in yeast. Thus, applications that result in the long term, repeated exposure of proteins containing yeast or yeast-like signatures, to human tissue are intensely scrutinized with respect to the potential of adverse immune reactions. This structure is also apt to cause dysfunction with respect to the protein=s natural activity and may also contribute to a shortened residence time in blood. In contrast, the mammary gland of pigs gives a glycosylation signature which more closely resembles that found in normal human blood proteins, helping to assure biochemical function and a long circulatory half-life.

The complex post-translational modifications of therapeutic proteins, such as those discussed above that are necessary for physiological activities, pose a difficult obstacle to the production of active vitamin K dependent proteins in cells using cloned genes. Moreover, attempts to culture genetically altered cells to produce VKD polypeptides have produced uneconomically low yields and, generally, preparations of low specific activity. Apparently, the post-translational modification systems in the host cells could not keep pace with production of exogenously encoded protein, reducing specific activity. Therefore, cell culture production methods have not provided the hoped for advantages for producing highly complex proteins reliably and economically.

An attractive alternative is to produce these complex proteins in transgenic organisms. However, it is likely that only mammals and perhaps birds will be able to carry out all the post-translational modifications necessary for their physiological function. It has not been possible, as yet, to produce commercially viable levels of certain complex polypeptides from a controlled source in a highly active form with a good yield, and there exists a need for better methods to produce such proteins.

An interesting new class of proteins, which is likely to be difficult to produce in commercial quantities in cell culture are the genetically engineered fusion, chimeric and hybrid molecules which are now being developed. These proteins are designed and produced by combining various domains or regions from different natural proteins, either wild type or mutated, which can confer the properties of each domain or region to the final hybrid molecule. An example of this is $X_{LC}LACI_{K1}$ (Girard, T. J., et al., Science 248, 1421-1424, 1990) which is a hybrid protein made up of domains from factor X and lipoprotein-associated coagulation inhibitor (LACI). LACI appears to inhibit tissue factor (TF)-induced blood coagulation by forming a quaternary inhibitory complex containing FXa, LACI, FVIIa and TF. $X_{LC}LACI_{K1}$ directly inhibits the activity of the factor VIIa-TF (tissue factor) catalytic complex, but is not dependent on FXa. Gamma-carboxylation of the FX portion of the hybrid protein is required for inhibitory activity. In order for efficient carboxylation to occur at high levels, it is likely that the propeptide of the recombinant VKD-protein must be properly matched to the endogenous carboxylase system (Stanley, T. B., et al, J. Biol. Chem., 274(24), 16940-16944, 1999). This is probably true for all VKD-polypeptides including chimeric ones such as $X_{LC}LACI_{K1}$. It appears that the endogenous carboxylase systems of any given species or tissue within that species, most of which are not identified or characterized, will differ in their compatibility to any given pro-peptide sequence. Also it is frequently desirable to have the propeptide cleaved from the nascent VKD protein, such as a $X_{LC}LACI_{K1}$ polypeptide, once gamma-carboxylation has been completed on the polypeptide's gla domain. It is therefore, also important to find a propeptide sequence that will be efficiently cleaved within the specific species and tissue in which it is being recombinantly produced. These factors render it problematic to find an expression system which can produce desirable amounts of biologically active VKD-proteins such as $X_{LC}LACI_{K1}$ chimeric proteins. In spite of being known as a potent coagulation inhibitor since the early 1990s, $X_{LC}LACI_{K1}$ chimeric molecules have not been made in large amounts in a commercially viable manner (ie., greater than 0.1 gm per liter per 24 hours) in recombinant mammalian cell culture. One way to improve expression of this protein in a transgenic system, particularly in transgenic pigs, may be to substitute the FIX propeptide sequence for the FX propeptide sequence, such a protein would be termed 9XKI.

New therapeutic molecules are being designed to have increased activity, decreased inactivation, increased half-life or specific activity and reduced immunogenicity and/or immunoreactivity to existing circulating antibodies in patients' bloodstreams. This has been demonstrated in genetically engineered Factor VIII proteins (U.S. Pat. No. 5,364,771, U.S. Pat. No. 5,583,209, U.S. Pat. No. 5,888,974, U.S. Pat. No. 5,004,803, U.S. Pat. No. 5,422,260, U.S. Pat. No. 5,451,521, U.S. Pat. No. 5,563,045). Mutations include deletion of the B domain (Lind, P., et al., Eur. J. Biochem. 232, 19-27, 1995), domain substitution or deletion, covalent linkage of domains, site-specific replacement of amino acids and mutation of certain cleavage sites. In particular, a genetically engineered inactivation-resistant factor VIII (IR8) has been developed to help in the treatment of hemophilia A (Pipe, S. W. and Kaufman, R. J., PNAS 94, 11851-11856, 1997). The introduction of specific sequences from porcine factor VIII can also be useful in the formation of a recombinant FVIII which is used to treat hemophiliacs with improved properties as stated above. These molecules can also be designed for improved expression. It is widely known that FVIII has restrictions in intracellular trafficking which lead to low levels of secretion. Modification of the domains associated with intracellular interactions with immunoglobulin binding protein (Bip) or calnexin would be examples of modifications used to improve secretory processing efficiency (Kaufman, R. J., Abstract S1-8, $10^{th}$ Int. Biotech. Symp., Sydney, Australia, 25-$30^{th}$ August, 1996). Factor VIII gDNA is another example of an extremely large and unwieldy DNA sequence (~110 kbp), whereas the cDNA is only 7 kbp, making it much more manageable.

Whey acidic protein (referred to as "WAP") is a major whey protein in the milk of mice, rats, rabbits and camels. The regulatory elements of the mouse WAP gene are entered in GenBank (U38816) and cloned WAP gene DNAs are available from the ATCC. The WAP promoter has been used successfully to direct the expression of many different heterologous proteins in transgenic animals for a number a years (EP0264166, Bayna, E. M. and Rosen, J. M., NAR, 18(10), 2977-2985, 1990). Lubon et al (U.S. Pat. No. 5,831,141) have used a long mouse WAP promoter (up to 4.2 kbp) to produce Protein C in transgenic animals. However, the longest rat WAP promoter that has been used is 949 bp (Dale, T. C., et al., Mol. Cell. Biol., 12(3), 905-914, 1992).

SUMMARY

The present invention is directed to producing transgenic proteins, compositions comprising transgenic proteins, transgenic organisms for making proteins, for modifying transgenic proteins in vivo, and to addressing the previously-discussed issues, e.g., as characterized in connection with the above-cited references each of which is incorporated by reference generally and more specifically as such teachings relate to methodology for related transgenic protein production and applications of such proteins.

In various embodiments of the present invention there is a composition for treating hemophilia B comprising a milk derivative containing recombinant human factor IX derived from a bodily fluid produced in a transgenic organism as described below.

In other more specific embodiments, the present invention is directed to a non-human transgenic mammal containing an exogenous DNA molecule stably integrated in its genome. The exogenous DNA molecule comprises: (a) a mammary gland-specific gene including a promoter; (b) a Factor IX-encoding DNA sequence that encodes the endogenous secretion-signal sequence, a Factor IX pro-sequence and a Factor IX sequence; (c) 3' regulatory sequences from a mammary gland-specific gene, which sequences are operatively linked to said Factor IX-encoding DNA sequence; (d) the stably integrated exogenous DNA does not include a WAP milk protein gene for providing gene rescue to achieve expression of the Factor 1×DNA; and (e) said Factor IX is secreted into the milk at least 220 micrograms Factor IX per milliliter of milk and is not activated by the milk-environment and therefore useable for Factor IX therapeutic applications.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention may be more completely understood in consideration of the detailed description of various embodiments of the invention in connection with the accompanying drawings, in which:

FIG. 1 is assembly of the plasmid pWAPFIX, according to an example embodiment of the present invention;

FIG. 2 is assembly of the plasmid pUCWAPFIX, according to another example embodiment of the present invention; and FIG. 3 is production of the modified plasmid pUCNot1, according to yet another example embodiment of the present invention.

FIG. 4 is the production of pUCWAP6, according to yet another example embodiment of the present invention.

While the invention is amenable to various modifications and alternative forms, specifics thereof have been shown by way of example in the drawings and will be described in detail. It should be understood, however, that the intention is not necessarily to limit the invention to the particular embodiments described. On the contrary, the intention is to cover all modifications, equivalents, and alternatives falling within the spirit and scope of the invention as defined by the appended claims.

DETAILED DESCRIPTION

As previously mentioned, the present invention is directed to products and approaches for regulating the expression of a protein in a transgenic organism, methods for obtaining polypeptides from transgenic organisms, compositions comprising transgenically produced polypeptides, and uses thereof. For example, one embodiment of the present invention is directed to a non-human transgenic mammal containing an exogenous DNA molecule that is stably integrated in its genome. The exogenous DNA molecule includes a mammary gland-specific gene, a Factor IX-encoding DNA sequence that performs encoding for applicable sequences, and 3' regulatory sequences from a mammary gland-specific gene. Surprisingly, in connection with the present invention, it has been discovered that, with the 5' and 3' regulatory sequences that are operatively linked to the Factor IX-encoding DNA sequence with the stably integrated exogenous DNA not including a WAP milk protein gene for providing gene rescue to achieve expression of the Factor IX DNA, the Factor IX can be made and secreted into the milk, so that the Factor IX containing milk can be made suitable for Factor IX therapeutic applications.

Methods for Making Transgenic Organisms

Transgenic organisms may be produced in accordance with the invention as described herein using a wide variety of well-known techniques, such as those described in Perry, M. M. and Sang, H. M., Transgenic Res. 2, 125-133; Ho Hong, Y. et al., Transgenic Res. 7(4), 247-252, 1998; Genetic Engineering Of Animals, Ed. A. Puhler, VCH Publishers, New York (1993) and in more detail in Volume 18 in Methods in Molecular Biology: Transgenesis Techniques, Eds. D. Murphy and D. A. Carter, Humana Press, Totowa, N.J. (1993); all of which are incorporated herein by reference in their entireties, particularly as to the foregoing in parts pertinent to methods for making transgenic organisms that express polypeptides. See also for instance Lubon et al., Transfusion Medicine Reviews X (2): 131-141 (1996) and Pursel, V. G., et al., 480 in the proceedings of 11th International Congress on Animal Reproduction and Artificial Insemination, Dublin, Ireland, 1988, which are incorporated herein by reference in their entirety, particularly as to the foregoing in parts pertinent to methods for making transgenic organisms.

In particular, transgenic mammals, such as mice and pigs, that express polypeptides in accordance with certain preferred embodiments of the invention, can be produced using methods described in among others Manipulating The Mouse Embryo, Hogan et al., Cold Spring Harbor Press (1986); Krimpenfort et al., Bio/Technology 9: 844 et seq. (1991); Palmiter et al., Cell 42: 343 et seq. (1985); Genetic Manipulation of the Early Mammalian Embryo, Kraemer et al., Cold Spring Harbor Press, Cold Spring Harbor, N.Y. (1985); Hammer et al., Nature 315: 680 et seq. (1985); U.S. Pat. No. 4,873,191 of Wagner et al. for Genetic Transformation of Zygotes, and U.S. Pat. No. 5,175,384 of Krimpenfort et al. for Transgenic Mice Depleted in Mature T-Cells and Methods for Making Transgenic Mice, each of which is incorporated herein by reference in its entirety, particularly as to the foregoing in parts pertinent to producing transgenic mammals by introducing DNA or DNA:RNA constructs for polypeptide expression into cells or embryos.

For example, transgenic organisms of the present invention can be produced by introducing into eggs, or developing embryos, one or more genetic constructs that engender expression of polypeptides as described herein. In certain preferred embodiments of the invention, DNAs that comprise cis-acting transcription controls for expressing a polypeptide operably linked to a region encoding the polypeptide are highly preferred. In other preferred embodiments a multigene system directing expression of a polypeptide and containing the DNA sequences coding for such a polypeptide, are highly preferred. Also highly preferred in this regard are single and or multi-gene constructs as described herein, that engender expression of genetically engineered genes for polypeptides. Constructs that comprise operable signal sequences that effectuate transport of the polypeptide product into a targeted compartment of an organism, such as a tissue or fluid, are further preferred in certain embodiments in this regard. Also especially preferred in this regard are constructs that are stably incorporated in the genome of germ line cells of the mature organism and inherited in normal, Mendelian fashion upon reproduction. One or more DNA or RNA:DNA hybrids or the like may be used alone or together to make transgenic organisms useful in the invention as described further below.

Standard, as well as unusual and new techniques for making transgenic organisms generally can be used to make transgenic organisms in accordance with the invention. Useful techniques in this regard include, but are not limited to, those that introduce genetic constructs by injection, infection, transfection—such as calcium phosphate transfection, using cation reagents, using sperm or sperm heads or the like—lipofection, liposome fusion, electroporation, and ballistic bombardment. Useful techniques include both those that involve homologous recombination, which can be employed to achieve targeted integration, and those that do not, such as those disclosed below.

Constructs can be introduced using these and other methods into differentiated cells, such as fibroblast cells, which are capable of being reprogrammed and then cloned, pluripotent cells, totipotent cells, germ line cells, eggs, embryos at the one cell stage, and embryos at several cell stages, among others, to make transgenic organisms of the invention. In these regards, among others, they may be introduced by such methods into pronuclear, nuclear, cytoplasmic or other cell compartments or into extracellular compartments of multicellular systems to make transgenic organisms of the invention.

In a preferred method, developing embryos can be infected with retroviral vectors and transgenic animals can be formed from the infected embryos. In a particularly preferred method DNAs in accordance with the invention are injected into embryos, at the single-cell or several cell stage. In some particularly preferred embodiments in this regard, DNA is injected into the pronucleus of a one-cell embryo. In other preferred embodiments in this regard. DNA is injected into the cytoplasm of a one-cell embryo. In yet another particularly preferred embodiment in this regard, DNA is injected into an early stage embryo containing several cells.

The following examples are provided merely to illustrate the invention, and are not to be interpreted as limiting the scope of the invention which is described in the specification and appended claims.

It is important to note that recombinant human Factor IX (rhFIX) and "FIX" made by a transgenic animal" are here terms for the same species. The Short WAP-FIX-cDNA is a genetic construct described below and is a term for the genetic construction using the 2.5 kbp fragment of the mouse WAP promoter operably linked to the cDNA of FIX. The Long WAP-FIX-cDNA is a genetic construct described below and is a term for the genetic construction using the 4.1 kbp fragment of the mouse WAP promoter operably linked to the cDNA of FIX.

Example 1

Construction and preparation of the 2.5 kbp WAP driven FIX-cDNA (short WAP-FIX-cDNA) construct to be used without gene rescue from a milk protein gene for microinjection into transgenic animals:

Generally, for achieving single gene expression systems for the transgenic animals described above, several parts of the entire murine WAP gene, which included the 2.5 kbp of 5'-untranslated promoter sequence and 3' untranslated regions (3'-UTR) were used and cloned by standard methods. See Campbell et al., *Nucleic Acids Res.* 12:8685 (1984). A cDNA fragment encoding human Factor IX was obtained such that the 3' untranslated region of the FIX cDNA was deleted. Using standard methods, an expression vector was constructed so that it contained a mouse WAP promoter, isolated as a 2.5 kbp EcoRI-KpnI fragment immediately 5' to the WAP signal sequence (the "short WAP promoter"), the human Factor IX cDNA (FIX-cDNA) sequence lacking a 3' untranslated region, and a 1.6 kbp fragment of the 3' untranslated region of the WAP gene. Expression vectors were amplified by bacterial transformation and purified from bacterial cultures using standard methods. Routine recombinant DNA techniques can be found, for example, in Sambrook et al., MOLECULAR CLONING, A LABORATORY MANUAL, Vol. 1-3 (Cold Spring Harbor Press 1989.

More specifically, a chimeric 2.5 kbp WAP 5'-promoter-Factor IX-3' WAP UTR construct was prepared, as follows:

Step 1: Production of pWAP4 "cassette vector"

Regulatory 5' and 3' flanking sequences of the mouse WAP gene were used as a source of the mammary specific expression system (Vector containing WAP gene a gift from Lothar Hennighausen, NIH). Specifically, a cassette vector containing a mouse WAP promoter, defined as a 2.5 kbp EcoRI-KpnI fragment (known as the "short WAP" promoter) immediately 5' to the WAP signal sequence and a 1.5 kbp fragment of the 3'-untranslated region of the WAP gene was prepared. These regulatory sequences do not include coding and intragenic untranslated sequences (introns) of the WAP gene. The vector designated pWAP4 was derived from pWAPPC3 (C. Russell, dissertation "Improvement of Expression of Recombinant Human Protein C in the Milk of Transgenic Mammal Using a Novel Transgenic Construct," Virginia Polytechnic Institute, Blacksburg, Va. (December 1993)) and was developed as follows: Using WAPPC3 as a template, PCR primers WAP3'S2 (which contains a 5'KpnI site and is homologous to endogenous WAP right after the stop signal) and WAP3'A1, were used to produce a segment with KpnI and BamHI sites on either end. This segment was digested with KpnI/BamHI and ligated with 68 bp containing the 5' end of the WAP 3' UTR KpnI\BamHI digested pWAPPC3 to remove the protein C coding region and insert an unique Kpn I cloning site. The ligation mixture was used to transform *E. coli* DH5α cells by electroporation with resultant colonies grown on LB ampicillin plates. Picked colonies were grown up in TB ampicillin broth, plasmids isolated and cut with KpnI, BamHI or both and subjected to gel electrophoresis. Sequencing was performed using WAP3'A1 primer and judged as being correct.

Step 2: The FIX cDNA (containing Kpn I sites located immediately before the start sequence and after the stop sequence) was generated as a PCR fragment. Fragment production protocol is as follows: 100 µl total volume containing 200 µM dNTP's, 0.5 µM of each primer (humFIX5'KpnI and humFIX3'KpnI, 2.5 units Pfu polymerase and 30 ng of plasmid template (pMCDSFIX obtained from Prof. Darryl Stafford, Department of Biology, University of North Carolina, Chapel Hill, N.C., USA), reaction mixture was subjected to 30 cycles of denaturation at 95° C. for 20 sec, annealing at 50° C. for 1 min and elongation at 75° C. for 5 min 45 sec. After cycling, the reaction mixture was subjected to blunting with T4 DNA polymerase for 10 min, EDTA concentration brought up to 25 mM, heated to 65° C. for 15 min, and extracted with Phenol:Chloroform (1:1), precipitated with equal volumes of 95% ethanol, aspirated, and resuspended in $H_2O$.

Step 3: Ligation, Transformation and Sequencing

The plasmid designated pUCFIX (See FIG. 1) containing the modified (Kpn I ends) FIX cDNA was produced by digestion of both pUC18 and the modified cDNA with Kpn I (per manufacturers instructions, Stratagene, La Jolla, Calif.) purification of digestion products by $CHCl_3$:Phenol (1:1) extraction, precipitation with equal volumes of 95% ethanol, aspiration and suspension in $H_2O$. Ligation of plasmid and cDNA was per manufacturers instructions (Stratagene) using 125 ng of Kpn I digested pUC18 and 125 ng of Kpn I digested modified cDNA. *E. coli* JM109 was transformed by electroporation using ligation mixture and plated on LB ampicillin plates. Selected colonies were grown up in TB ampicillin broth. Plasmid preparations from these colonies were analyzed by restriction enzyme digestion (Kpn I) and gel electrophoresis. The entire sense strand of the cDNA was sequenced and found to be correct as compared with FIXA sequences located in Genebank.

Step 4: Introduction of FIX cDNA into pWAP4 "cassette vector" to produce pWAPFIX Both pWAP4 and pUCFIX (FIG. 1) were digested with Kpn I in separate reactions, subjected to gel electrophoresis and the appropriate plasmid fragments removed from the gel and ligated. *E. coli* JM109 was transformed by electroporation using ligation mixture and plated on LB ampicillin plates. Selected colonies were grown up in TB ampicillin broth. Plasmid preparations from these colonies were analyzed by restriction enzyme digestion (Kpn I) then gel electrophoresis. Clones positive for the insert were subjected to PCR analysis using primers FIXS1 and WAP3'A1 to determine the correct orientation of the insert. The correct plasmid is identified as pWAPFIX. The insert WAPFIX was removed from pWAPFIX by endonuclease digestion with EcoRI, gel purified and ligated into EcoRI digested pUC18 in order to switch the bacterial vector from pBS to pUC18. The new plasmid was designated pUCWAPFIX (FIG. 2).

Step 5: Preparation of Short WAP FIX-cDNA for Microinjection

The short WAP-FIX-cDNA (WAPFIX) construct as described above that excised from pUCWAPFIX by EcoRI endonuclease digestion was purified for microinjection as follows. After cleaving the construct from its vector, the solution was brought to 10 mM magnesium, 20 mM EDTA and 0.1% SDS and then extracted with phenol/chloroform (1:1). DNA was precipitated from the aqueous layer with 2.5 volumes of ethanol in the presence of 0.3 M sodium acetate at −20° C. overnight. After centrifugation, the pellet was washed with 70% ethanol, dried, and resuspended in sterile distilled water. The extracted DNA was purified by standard NaCl gradient ultracentrigation. DNA concentrations were determined by agarose gel electrophoresis by staining with ethidium bromide and comparing the fluorescent intensity of an aliquot of the DNA with the intensity of standards. Samples were then adjusted to 10 µg/ml and stored at −20° C., prior to microinjection. Unlike the examples of Clark et al., U.S. Pat. No. 5,714,345 and Van Cott et al., Genetic Analysis: Biomolecular Engineering 15 (1999) 155-160, no co-injection of a milk gene is done with the FIX containing construct. Thus, no other milk protein gene that could be used to perform "gene rescue" on the WAP5FIX construct was used; in addition to the buffer components, the microinjection mixture contained only the Short WAP-FIXcDNA construct DNA.

Example 2

Production of transgenic pigs that express the Short FIX-cDNA without "gene rescue" from a milk protein gene.

Step 1: Pig embryos are recovered from the oviduct and placed into a 1.5 ml microcentrifuge tube containing approximately 0.5 ml embryo transfer media (Beltsville Embryo Culture Medium). Embryos are centrifuged for 12 minutes at 16,000×g RCF (13,450 RPM) in a microcentrifuge (Hermle, model Z231). The embryos are then removed from the microfuge tube with a drawn and polished Pasteur pipette and placed into a 35 mm petri dish for examination. Embryos are then placed into a microdrop of media (approximately 100 µl) in the center of the lid of a 100 mm petri dish, and silicone oil was used to cover the microdrop and fill the lid to prevent media from evaporating. The petri dish lid containing the embryos is set onto an inverted microscope (Carl Zeiss) equipped with both a heated stage and Hoffman Modulation Contrast optics (200× final magnification). A finely drawn (Kopf Vertical Pipette Puller, model 720) and polished (Narishige microforge, model MF-35) micropipette is used to stabilize the embryos while about 1-2 picoliters of purified DNA solution (10 µg/ml) containing only short WAP-FIX-cDNA genetic constructs without milk proteins for cDNA gene rescue was delivered to non-pronuclear one-cell or two-cell pig embryos using another finely drawn micropipette. Embryos surviving the microinjection process as judged by morphological observation are loaded into a polypropylene tube (2 mm ID) for transfer into the recipient pig. About 40-50 microinjected embryos are transferred into each hormonally synchronized surrogate mother recipient female pig.

Step 2: Determination of transgenic piglets born from microinjection of 1-cell and two-cell pig embryos.

The gestation time of recipient female pigs is about 114 days. About 4 to 11 piglets are born in each litter. To determine whether test animals carried the recombinant constructs, tissue samples were removed from transgenic animals and DNA isolated. DNA is isolated by digesting tissue in (50 mM Tris-HCl, 0.15 M NaCl, 1 M $Na_2ClO_4$, 10 mM EDTA, 1% sodium dodecylsulfate, 1% 2-mercaptoethanol, 100 ug/ml proteinase K, pH 8.0). 750 ul of lysate was extracted with 250 ul chloroform/phenol (1:1) followed by precipitation with isopropanol 0.7 volumes, washed in 70% ethanol and dried. DNA is suspended in TE (10 mM Tris-HCl and 1 mM EDTA pH 8.0). Swine produced after embryo transfer of microinjected embryos were screened by Southern analysis. 10 μg of DNA isolated from tail tissue is digested with the endonuclease Pst I an subjected to agarose gel electrophoresis and transferred to a nylon membrane. The membrane is probed with a $^{32}P$ labeled DNA fragment of the WAP promoter consisting of the Not I to Pst I (~2.0 kbp) 5' fragment. Hybridization is carried out at 68° C. for 4 hours using Quick Hyb (Stratagene; LaJolla, Calif.). Following standard washing methods, the membrane is subjected to autoradiography (−70° C.) for a period of 24 hours. Observance of a 2.0 kbp band indicated the presence of the transgene. To confirm the presence of the Factor IX cDNA, 10 μg of DNA isolated from tail tissue is digested with the endonuclease BamHI an subjected to agarose gel electrophoresis and transferred to a nylon membrane. The membrane is probed with a $^{32}P$ labeled DNA fragment of the FIX cDNA consisting of the whole cDNA Kpn I to Kpn I (~1.4 kbp). Hybridization is carried out at 68° C. for 4 hours using Quick Hyb (Stratagene; LaJolla, Calif.). Following standard washing methods, the membrane is subjected to autoradiography (−70° C.) for a period of 24 hours. Observance of a ~5.5 kbp band indicates the presence of the short WAP-FIX-cDNA transgene.

Step 3: Collection and storage of milk from transgenic pigs containing short WAP-FIX-cDNA without "gene rescue" from a milk protein gene.

Lactating sows are injected intramuscularly with 30-60 IU of oxytocin (Vedco Inc., St. Joseph, Mo.) to stimulate milk let-down. Letdown occurs two to five minutes after injection. Pigs are milked by hand during the course of this study. Immediately after collection the milk is diluted 1:1 with 200 mM EDTA, pH 7.0 to solubilize the caseins and then frozen. Small aliquots (about one milliliter) of the milk/EDTA mixture are taken and centrifuged for approximately 30 minutes at 16000×g at 4° C. The fat layer is separated from the diluted whey fraction, and the diluted whey fraction is used for all further assays.

Step 4: Detection of high levels of recombinant human FIX in milk of transgenic pigs containing short WAP-FIX-cDNA without the use of "gene rescue" from a milk protein gene.

Data from milk samples that are processed to diluted whey samples are interpreted multiplied by a factor of 1.9 to account for dilution with EDTA and subsequent removal of milk fat. Amounts of Factor IX in milk are measured by polyclonal ELISA. Briefly, Immulon II microtiter plates (Fisher Scientific, Pittsburgh) are coated overnight with 100 μl/well of 1:1000 rabbit anti-human Factor IX (Dako) in 0.1 M $NaHCO_3$, 0.1 M NaCl, pH 9.6 at 4° C. The wells are washed with TBS-Tween (TBST, 25 mM Tris, 50 mM NaCl, 0.2% Tween 20, pH 7.2), and then blocked for 30 minutes with TBS/0.1% BSA at room temperature. Samples and human Factor IX standard derived from plasma in the TBS-BSA dilution buffer are added in triplicate to the wells (100 μl/well) and incubated at 37° C. for 30 minutes. The wells are then washed and blocked for another 10 minutes at room temperature. Sheep anti-human Factor 1:1000 in TBS-BSA, is then incubated in the wells for 30 minutes at 37° C., followed by anti-sheep IgG/HRP (Sigma, St. Louis). Bound chromophore is detected with OPD substrate (Abbott, Chicago) at 490 nm using an EL308 Bio-Tek Microplate reader. Daily expression levels of FIX are about 100-500 μg/ml milk and this is maintained throughout 50-60 day lactation.

Step 5: Western analysis of the high level expression of recombinant human FIX in milk of transgenic pigs containing short WAP-FIX-cDNA without the use of "gene rescue" from a milk protein gene.

Recombinant human Factor IX (rhFIX) also is examined using Western Blot Analysis. Daily samples of EDTA-diluted whey as prepared above and taken from transgenic short WAP-FIXcDNA pigs are electrophoresed on 8-16% SDS gels (Novex, San Diego). Approximately 125 ng of recombinant human Factor IX (as determined by polyclonal ELISA) and human Factor IX standard derived from plasma are loaded in each lane. A total of 25 μg of total protein from a pool of non-transgenic (NTG) whey is loaded on the gels. After electrophoresis, proteins are transferred overnight to PVDF membranes (Bio Rad). The membranes are washed for 30 minutes in TBST, blocked with TBS/0.05% Tween 20/0.5% Casein (TBST-Casein). The membranes are developed with rabbit anti-Factor IX (Dako) (1:1000 in TBST-Casein for 45 minutes at 37° C.), followed by anti-rabbit IgG/HRP (Sigma) (1:1000 in TBST-Casein for 45 minutes at 37° C.), and the DAB metal enhanced staining (Pierce). Molecular weight markers are purchased from Bio-Rad. The presence of about 100-500 ug/ml of rhFIX in the milk of transgenic pigs containing the short WAP-FIX-cDNA without benefit of the gene rescue by a milk protein gene is detected by the Western Blot Analysis.

Example 3

Purification of high levels of recombinant human FIX (rhFIX) in milk of transgenic pigs containing short WAP-FIX-cDNA having achieved high expression of rhFIX without the use of "gene rescue" from a milk protein gene.

Recombinant human Factor IX is purified from whey derived from a pool consisting of milk taken from 50-60 days of the first lactation of a short WAP-FIX-cDNA transgenic pig. The first step consisted of ion exchange chromatography followed by metal-dependent immunoaffinity chromatography using a monoclonal antibody designated as MAb1H5. In these studies, all columns and buffers are kept at 4° C. A pool of daily EDTA-expanded whey samples is diluted to OD 280 μm of 5.0 with TBS, pH 7.2, then loaded at 1 cm/min on DEAE FF Sepharose. The column is washed with TBS, pH 7.2, and then eluted with 0.25 M NaCl in TBS. This fraction is diluted 1:1 with 40 mM $MgCl_2$ in TBS to a final concentration of 20 mM $MgCl_2$ and loaded on a 1H5 MAb column. The column is washed with TBS containing 20 mM $MgCl_2$, and the product is eluted with 20 mM citrate, 0.15 M NaCl, pH 6.8. The product is dialyzed overnight against 10 mM imidazole, pH 7.2.

Example 4

Determination of the biological activity of immunopurified recombinant Human Factor IX (rhFIX) processed from milk of transgenic pigs containing short WAP-FIX-cDNA having achieved high level expression of rhFIX without using "gene rescue" from a milk protein gene.

The biological activity of the purified recombinant human Factor IX from a transgenic pig is measured using a one-stage activated partial thromboplastin clotting time assay (APTT) clotting assay following a protocol given by the American Red Cross Plasma Derivatives Laboratory (Procedure for Factor IX Coagulation Assay, March 1992). Briefly, each well of a plastic Coag-a-mate tray receives 90 µl of Factor IX-deficient plasma plus 10 µl of a Factor IX standard or sample, diluted with Tris/saline/BSA. The tray is then placed on an automated analyzer (APTT mode, 240 second activation). The run is started, which automatically performed the addition of 100 µl of APTT reagent and 100 µl of 0.025 M $CaCl_2$. Data obtained using a standard Factor IX preparation are fitted to the equation y−ax+b where y=clotting time and x=Factor IX, which is then used to determine the amount of Factor IX in a sample. The Standards of normal plasma reference pool (Sigma) and human Factor IX derived from plasma are used in the assay. Duplicates of the immunopurified recombinant human Factor IX, human Factor IX, and normal plasma reference pool samples are run at each dilution. The immunopurified recombinant human Factor IX had a specific activity of about 200-350 U/mg, which is comparable to the immunopurified human Factor IX from plasma which had a specific activity of 200-230 U/mg, with the normal plasma reference pool activity being defined as 250 U/mg.

Example 5

A milk derivative of a recombinant Human Factor IX (rhFIX) processed from milk of transgenic pigs containing short WAP-FIX-cDNA having high level expression of rhFIX achieved without using "gene rescue" from a milk gene.

A milk derivative concentrate of recombinant human FIX (rhFIX) useful for oral delivery of rhFIX is made from the milk of a transgenic pig containing a transgene composed of the 2.5 kbp mouse whey acidic protein promoter (WAP), the cDNA encoding human FIX, and a 1.6 kbp fragment of the 3' UTR of WAP. The expression level is about 0.1-0.5 g/l of rhFIX. Greater than about 80% of the rhFIX is biologically active. The skim milk is treated with a chelating agent such as 100 mM EDTA pH 7.5 or 100 mM Sodium Citrate pH 6.5 to clarify the milk of casein micelles. The clarified whey is passed over a DEAE-Sepharose or DEAE-Cellulose chromatographic column and the rhFIX is adsorbed. This adsorbed rhFIX is selectively desorbed from the anion exchange column using 15 mM $Ca^{2+}$ Tris-buffered-saline 150 mM NaCl (TBS). This eluted fraction of rhFIX containing selected, highly biologically active fractions of rhFIX is useful for oral delivery of rhFIX for therapeutic treatment of hemophilia B patients is passed through a 0.2 micron filter top remove bacterial contamination and then lyophilized to a powder. The rhFIX in the DEAE-column eluate has a composition that is volume reduced and concentrated by 25 to 50-fold over that of starting skim milk.

Example 6

A therapeutic application achieving oral delivery of the recombinant Human Factor IX (rhFIX) using a milk derivative made from the milk of transgenic pigs containing short WAP-FIX-cDNA having high level expression of rhFIX achieved without using "gene rescue" from a milk protein gene.

The lyophilized powder of example 5 is reconstituted with aqueous containing ordinary bovine milk cream such as to restore the volume to 25 to 50-fold concentrate over that of the original whey. The mixture is fed to hemophilia type B mice shortly after their first meal post sleep where less than 1 ml is fed to each mouse. The bleeding time by measured tail incision is measured 12 hours later. The corrected bleeding time is 5-7 minutes as compared to 11 minutes for a control hemophiliac mouse who was not fed the rhFIX milk concentrate and 5 minutes for a normal mouse with normal hemostasis.

Example 7

A therapeutic application achieving oral immunotolerization of recombinant Human Factor IX (rhFIX) derived from Chinese Hamster Ovary cells using a milk derivative containing rhFIX made from milk of transgenic pigs containing short WAP-FIX-cDNA having high level expression of rhFIX achieved without using "gene rescue" from a milk protein gene.

Mice are fed the reconstituted mixture from example 6 everyday consecutively for one month and after this month, they are sensitized with complete Freund's adjuvant and recombinant human Factor IX. After 12 days, blood samples from these mice do not respond with the presence of anti-human FIX antibodies and also does not respond with T-cells which are activated by the presence of recombinant FIX derived from Chinese Hamster ovary cells. Control mice that have not been fed the mixture from example 12 are sensitized with the same adjuvant and human FIX mixture. After 12-14 days the blood of these human FIX sensitized control mice exhibit a strong immunological response consisting of both anti-human FIX antibodies and T-cells that are activated by the presence of human FIX.

Example 8

A therapeutic application achieving oral immunotolerization of recombinant Human Factor IX (rhFIX) using a milk derivative having the same rhFIX that is made from milk of transgenic pigs containing short WAP-FIX-cDNA having high level expression of rhFIX achieved without using "gene rescue" from a milk protein gene.

Mice are fed the reconstituted mixture from example 6 everyday consecutively for one month and after this month, they are sensitized with complete Freund's adjuvant and recombinant human Factor IX. After 12 days, blood samples from these mice do not respond with the presence of anti-human FIX antibodies and also do not respond with T-cells which are activated by the presence of recombinant FIX derived from the milk of transgenic pigs. Control mice that have not been fed the mixture from example 12 are sensitized with the same adjuvant and human FIX mixture. After 12-14 days the blood of these human FIX sensitized control mice exhibit a strong immunological response consisting of both anti-human FIX antibodies and T-cells that are activated by the presence of human FIX.

Example 9

A therapeutic application achieving oral immunotolerization of Human Factor IX derived from plasma using a milk derivative containing rhFIX made from milk of transgenic pigs containing short WAP-FIX-cDNA having high level expression of rhFIX achieved without using "gene rescue" from a milk protein gene.

Mice are fed the reconstituted mixture from example 6 everyday consecutively for one month and after this month, they are sensitized with complete Freund's adjuvant and recombinant human Factor IX. After 12 days, blood samples from these mice do not respond with the presence of anti-human FIX antibodies and also do not respond with T-cells which are activated by the presence of human FIX. Control mice that have not been fed the mixture from example 12 are sensitized with the same adjuvant and human FIX mixture. After 12-14 days the blood of these human FIX sensitized control mice exhibit a strong immunological response consisting of both anti-human FIX antibodies and T-cells that are activated by the presence of human FIX.

Example 10

Construction and preparation of the 4.1 kb WAP driven FIX-cDNA (long WAP-FIX-cDNA) construct for microinjection into embryos to make transgenic animals having high level expression of FIX achieved without using "gene rescue" from a milk gene.

Step 1: Generally, the entire murine WAP gene was cloned by standard methods, as described above in Example 1, and the regulatory 5' and 3' UTR-flanking sequences of the mouse WAP gene were used for mammary specific expression (Gift from Lothar Hennighausen NIH). Specifically, a cassette vector (pUCWAP6) containing a "long WAP" promoter, defined as a 4.1 kbp Not I-Kpn I fragment immediately 5' to the WAP signal sequence and a 1.6 kbp fragment of the 3' untranslated region of the WAP gene was prepared. These regulatory sequences do not include coding and intragenic untranslated sequences (introns) of the mWAP gene. The development of pUCWAP6 was as follows: The pUC18 vector (Invitrogen) was cut with the enzymes EcoRI and Hind III to remove the multiple cloning site of the vector, blunted with exonuclease and ligated with Not I linkers. The plasmid was then cut with Not I and ligated. Ligation mixture was used to transform *E. coli* DH5α cells on LB ampicillin plates, picked colonies were grown in TB ampicillin broth, plasmids were isolated and cut with Not I then subjected to gel electrophoresis. Plasmid was judged to be correct and designated as pUCNotI (See FIG. 3). The vector pWAP4 (described above) was digested with EcoRI and the fragment containing the WAP 5'-2.5 kbp promoter and 3'-UTR genetic elements were separated by gel electrophoresis and purified. The ends of the fragment were modified by blunting with exonuclease and Not I linkers were ligated on. The fragment was cut with Not I and ligated into the Not I restriction site of pUCNotI then used to transform *E. coli* DH5α cells on ampicillin plates. Picked colonies were grown in TB ampicillin broth. The Isolated plasmid was verified to be correct by Not I digestion with the plasmid being designated pUCWAP5. The pUC WAP5 plasmid was subjected to Kpn I digestion and a partial Not I digestion producing a fragment that contained the pUC-NotI vector sequence flanked by the mWAP 3'-UTR. This fragment was ligated with the 4.1 kb 5'-WAP promoter produced from digestion of p227.6 (gift from American Red Cross) with NotI, KpnI and Hind III. The ligation mixture was then used to transform *E. coli* JM109 cells that were grown on LB ampicillin plates picked colonies were grown in TB ampicillin broth, plasmids isolated were cut with Not I, and NotI/KpnI and judged to be correct. The plasmid was then designated pUCWAP6 (See FIG. 4).

Step 2: Production of pUCWAP6FIX

The plasmid pUCWAP6FIX was produced by digestion of pUCWAPFIX with Kpn I and isolating the FIX cDNA by gel electrophoresis. This fragment was purified using a gel extraction kit (Qiagen; Valencia, Calif.) and inserted into the KpnI site of pUCWAP6 after Kpn I digestion and both fragments were then subjected to ligation. The ligation mixture was then used to transform *E. coli* JM109 cells that were then plated on LB ampicillin plates. Picked colonies were grown in TB ampicillin broth and plasmids were isolated. Isolated plasmids were digested with Nsi I to verify orientation of the cDNA insert. Plasmids that contained the insert in the correct orientation were designated pUCWAP6FIX. After insert confirmation, large scale purification was undertaken, according to methods well known in the art. This is termed the "long WAP-FIX-cDNA".

Step 3: Preparation of Long WAP-FIX-cDNA for Microinjection

The Long WAP-FIX-cDNA constructed as described in the above in steps was excised from pUCWAP6FIX by Not I endonuclease digestion and purified for microinjection as follows. After cleaving a WAP6FIX from its vector, DNA was purified by standard NaCl gradient ultracentrigation. DNA concentrations were determined by agarose gel electrophoresis by staining with ethidium bromide and comparing the fluorescent intensity of an aliquot of the DNA with the intensity of standards. Samples were then adjusted to 10 µg/ml and stored at −20° C., prior to microinjection. No other milk protein gene that could be used to perform gene rescue for this Long WAP-FIXcDNA construct was used; in addition to the buffer components, the microinjection mixture contained only the Long WAP-FIXcDNA construct DNA.

Example 11

Production of Long WAP-FIX-cDNA transgenic mice having high level expression of rhFIX achieved without using "gene rescue" from a milk gene.

Step 1: Transgenic mice were produced essentially as described by Hogan et al., *Manipulating the Mouse Embryo*, Cold Spring Harbor Press, (1986), which is hereby incorporated by reference. That is, glass needles for micro-injection were prepared using a micropipet puller and microforge. Injections were performed using a Nikon microscope having Hoffman Modulation Contrast optics, with Narashigi micromanipulators and a pico-injector driven by N2 (Narashigi). Fertilized mouse embryos were surgically removed from oviducts of superovulated female CD-1 mice and placed into M2 medium. Cumulus cells were removed from the embryos with hyaluronidase at 300 µg/ml. The embryos were then rinsed in new M2 medium, and stored at 37 degrees centigrade prior to injection. Stock solutions containing about 5 µg/ml of the above described DNA were prepared and microinjected into non-pronuclear mouse embryos. After injecting the DNA, embryos were implanted into avertin-anesthesized CD-1 recipient females made pseudo-pregnant by mating with vasectomized males. About 25-30 microinjected mouse embryos per recipient were transferred into pseudopregnant females.

Step 2: DNA was isolated by digesting tissue in (50 mM Tris-HCl, 0.15 M NaCl, 1 M $Na_2$ $ClO_4$, 10 mM EDTA, 1% sodium dodecylsulfate, 1% 2-mercaptoethanol, 100 ug/ml proteinase K, pH 8.0). 750 ul of lysate was extracted with 250 ul chloroform/phenol (1:1) followed by precipitation with isopropanol 0.7 volumes, washed in 70% ethanol and dried. DNA was suspended in TE (10 mM Tris-HCl and 1 mM EDTA pH 8.0). Mice produced after embryo transfer of microinjected embryos were screened by Southern analysis. To confirm the presence of the Factor IX cDNA. 10 µg of DNA isolated from tail tissue was digested with the endonuclease BamHI an subjected to agarose gel electrophoresis and transferred to a nylon membrane. The membrane was probed with a $^{32}$P labeled DNA fragment of the FIX cDNA consisting of the whole cDNA Kpn I to Kpn I (~1.4 kbp). Hybridization was carried out at 68° C. for 4 hours using Quick Hyb (Stratagene; LaJolla, Calif.). Following standard washing methods, the membrane was subjected to autoradiography (−70° C.) for a period of 24 hours. Observance of a ~7.1 kbp band indicated the presence of the whole transgene.

Example 12

Western Analysis of high level expression of recombinant human FIX in milk of transgenic mice containing long WAP-FIX-cDNA achieved without using gene rescue from a milk protein gene.

Recombinant human Factor IX from the milk of transgenic mice having the long WAP-FIX-cDNA (without gene rescue from a milk protein gene) was examined using Western analysis. Daily samples of EDTA-diluted whey as prepared above and taken from transgenic short WAP-FIXcDNA pigs were electrophoresed on 8-16% SDS gels (Novex, San Diego). Approximately 125 ng of recombinant human Factor IX (as determined by polyclonal ELISA) and human Factor IX standard derived from plasma were loaded in each lane. A total of 25 μg of total protein from a pool of non-transgenic (NTG) whey was loaded on the gels. After electrophoresis, proteins were transferred overnight to PVDF membranes (Bio Rad). The membranes were washed for 30 minutes in TBST, blocked with TBS/0.05% Tween 20/0.5% Casein (TBST-Casein). The membranes were developed with rabbit anti-Factor IX (Dako) (1:1000 in TBST-Casein for 45 minutes at 37° C.), followed by anti-rabbit IgG/HRP (Sigma) (1:1000 in TBST-Casein for 45 minutes at 37° C.), and the DAB metal enhanced staining (Pierce). Molecular weight markers were purchased from Bio Rad. Western analyses revealed the presence of three sub-populations of recombinant human Factor IX in transgenic mouse derived samples: the major population migrated at a $M_r$ of about 60-65 kDa, which is a slightly lower $M_r$ than human Factor IX, and minor sub-populations migrated at about 40-45 kDa, and at about 25 kDa. Plasma human Factor IX also possessed a subpopulation at about 45-50 kDa. The transgenic mouse milk samples were estimated to contain about 1 to 2 g/l of rhFIX.

Example 13

Production of transgenic pigs that express the long WAP-FIX-cDNA at very high levels achieved without using "gene rescue" from a milk protein gene.

Step 1: Pig embryos were recovered from the oviduct, and were placed into a 1.5 ml microcentrifuge tube containing approximately 0.5 ml embryo transfer media (Beltsville Embryo Culture Medium). Embryos were centrifuged for 12 minutes at 16,000×g RCF (13,450 RPM) in a microcentrifuge (Hermle, model Z231). The embryos were then removed from the microcentrifuge tube with a drawn and polished Pasteur pipette and placed into a 35 mm petri dish for examination. Embryos were then placed into a microdrop of media (approximately 100 μl) in the center of the lid of a 100 mm petri dish, and silicone oil was used to cover the microdrop and fill the lid to prevent media from evaporating. The petri dish lid containing the embryos was set onto an inverted microscope (Carl Zeiss) equipped with both a heated stage and Hoffman Modulation Contrast optics (200× final magnification). A finely drawn (Kopf Vertical Pipette Puller, model 720) and polished (Narishige microforge, model MF-35) micropipette was used to stabilize the embryos while about 1-2 picoliters of stock solution containing about 10 μg/ml of the above described DNA was microinjected into the nonpronuclear stage pig embryos using another finely drawn micropipette. Embryos surviving the microinjection process as judged by morphological observation were loaded into a polypropylene tube (2 nun ID) for transfer into the recipient pig. About 40-50 microinjected embryos were transferred into each hormonally synchronized surrogate mother recipient female pig.

Step 2: Determination of transgenic piglets born from microinjection of pig embryos.

DNA was isolated by digesting tissue in (50 mM Tris-HCl, 0.15 M NaCl, 1 M Na$_2$ ClO$_4$, 10 mM EDTA, 1% sodium dodecylsulfate, 1% 2-mercaptoethanol, 100 ug/ml proteinase K, pH 8.0). 750 ul of lysate was extracted with 250 ul chloroform/phenol (1:1) followed by precipitation with isopropanol 0.7 volumes, washed in 70% ethanol and dried. DNA was suspended in TE (10 mM Tris-HCl and 1 mM EDTA pH 8.0). Pigs produced after embryo transfer of microinjected embryos were screened by Southern analysis. To confirm the presence of the Factor IX cDNA. 10 μg DNA isolated from tail tissue was digested with the endonuclease BamHI an subjected to agarose gel electrophoresis and transferred to a nylon membrane. The membrane was probed with a $^{32}$P labeled DNA fragment of the FIX cDNA consisting of the whole cDNA Kpn I to Kpn I (~1.4 kbp). Hybridization was carried out at 68° C. for 4 hours using Quick Hyb (Stratagene; LaJolla, Calif.). Following standard washing methods, the membrane was subjected to autoradiography (−70° C.) for a period of 24 hours. Observance of a ~7.1 kbp band indicated the presence of the entire long WAP-FIX-cDNA transgene.

Step 3: Collection and storage of milk from transgenic pigs containing Long WAP-FIX-cDNA without using "gene rescue" by a milk protein gene.

Lactating sows were injected intramuscularly with 30-60 IU of oxytocin (Vedco Inc., St. Joseph, Mo.) to stimulate milk let-down. Letdown occurred two to five minutes after injection. Pigs were milked by hand during the course of this study. Immediately after collection the milk was diluted 1:1 with 200 mM EDTA, pH 7.0 to solubilize the caseins and then frozen. Small aliquots (about one milliliter) of the milk/EDTA mixture were taken and centrifuged for approximately 30 minutes at 16000×g at 4° C. The fat layer was separated from the diluted whey fraction, and the diluted whey fraction was used for all further assays.

Step 4: Detection of recombinant human fix in milk of transgenic pigs containing Long WAP-FIX-cDNA without using "gene rescue" by a milk protein gene.

Data from milk samples that were processed to diluted whey samples were adjusted by a factor of 1.9 to account for dilution with EDTA and subsequent removal of milk fat. Amounts of Factor IX in milk were measured by polyclonal ELISA. Briefly, Immulon II microtiter plates (Fisher Scientific, Pittsburgh) were coated overnight with 100 μl/well of 1:1000 rabbit anti-human Factor IX (Dako) in 0.1 M NaHCO$_3$, 0.1 M NaCl, pH 9.6 at 4° C. The wells were washed with TBS-Tween (TBST, 25 mM Tris, 50 mM NaCl, 0.2% Tween 20, pH 7.2), and then blocked for 30 minutes with TBS/0.1% BSA at room temperature. Samples and human Factor IX standard derived from plasma in the TBS-BSA dilution buffer were added in triplicate to the wells (100 μl/well) and incubated at 37° C. for 30 minutes. The wells were then washed and blocked for another 10 minutes at room temperature. Sheep anti-human Factor IX 1:1000 in TBS-BSA, was then incubated in the wells for 30 minutes at 37° C., followed by anti-sheep IgG/HRP (Sigma, St. Louis). Bound chromophore was detected with OPD substrate (Abbott, Chicago) at 490 nm using an EL308 Bio-Tek Microplate reader. Daily expression levels of about 2000-5000 µg/ml milk were maintained throughout 50-60 day lactation.

Step 5: Western analysis of high level expression of recombinant human FIX (rhFIX) in milk of transgenic pigs containing long WAP-FIX-cDNA without using "gene rescue" by a milk protein gene.

Recombinant human Factor IX also was examined using Western analysis. Daily samples of EDTA-diluted whey as prepared above and taken from transgenic Long WAP-FIX-cDNA pigs were electrophoresed on 8-16% SDS gels (Novex, San Diego). Approximately 125 ng of recombinant human Factor IX (as determined by polyclonal ELISA) and human Factor IX standard derived from plasma were loaded in each lane. A total of 25 µg of total protein from a pool of non-transgenic (NTG) whey was loaded on the gels. After electrophoresis, proteins were transferred overnight to PVDF membranes (Bio Rad). The membranes were washed for 30 minutes in TBST, blocked with TBS/0.05% Tween 20/0.5% Casein (TBST-Casein). The membranes were developed with rabbit anti-Factor IX (Dako) (1:1000 in TBST-Casein for 45 minutes at 37° C.), followed by anti-rabbit IgG/HRP (Sigma) (1:1000 in TBST-Casein for 45 minutes at 37° C.), and the DAB metal enhanced staining (Pierce). Molecular weight markers were purchased from Bio Rad. Western analyses revealed the presence of three sub-populations of recombinant human Factor IX: the major population migrated at a $M_r$ of about 60-65 kDa, which is a slightly lower $M_r$ than human Factor IX, and minor sub-populations migrated at about 40-45 kDa, and at about 25 kDa. Plasma human Factor IX also possessed a subpopulation at about 45-50 kDa. The concentration of rhFIX in milk was estimated to be about 2 g/l or more.

Example 14

Purification of recombinant human FIX in milk of transgenic pigs containing Long WAP-FIX-cDNA having high level expression of FIX achieved without using "gene rescue" from a milk gene.

Recombinant human Factor IX (rhFIX) was purified from whey derived from a pool consisting of milk taken from 50-60 days of the first lactation of a Long WAP-FIX-cDNA transgenic pig. The first step consisted of DEAE exchange chromatography, followed by hydrophobic interaction chromatography, followed by chromatographic adsorption onto Q-Sepharose anion exchange matrix by $Ca^{2+}$-specific elution. In these studies, all columns and buffers were kept at 4° C. A pool of daily EDTA-expanded whey samples was diluted to OD 280 nm of 5.0 with TBS, pH 7.2, then loaded at 1 cm/min on DEAE FF Sepharose. The column was washed with TBS, pH 7.2, and then eluted with 0.25 M NaCl in TBS. The rhFIX was eluted from the DEAE-Sepharose using 300 mM NaCl in TBS. This rhFIX containing eluate was dialyzed to TBS and loaded onto Q-Sepharose. The rhFIX was eluted from the Q-Sepharose column using 15 mM $CaCl_2$ ($Ca^{2+}$) in TBS. The rhFIX containing eluate from the Q-Sepharose eluate was rendered 1 M NaCl. The rhFIX passes through the Butyl-column unabsorbed. The unabsorbed material from the Butyl-Sepharose column containing the rhFIX is dialyzed against TBS to remove the majority of casein milk protein contaminants. The dialyzed rhFIX containing fraction in TBS is adsorbed to Q-Sepharose and eluted in a sequence of 5 mM $Ca^{2+}$, 10 mM $Ca^{2+}$, 15 mM $Ca^{2+}$, and 2 M NaCl in TBS buffers. The chromatographic procedure isolated in these fractions contained rhFIX to about 80% or higher purity as judged by silver-stained SDS-PAGE.

Example 15

Determination of the biological activity of purified rhFIX processed from milk of transgenic pigs containing Long WAP-FIX-cDNA having high level expression of FIX achieved without using "gene rescue" from a milk protein gene.

The biological activity of the recombinant human Factor IX purified from the milk of Long WAP-FIX-cDNA pigs described in Example 14 is measured using a one-stage activated partial thromboplastin clotting time assay (APTT) clotting assay following a protocol given by the American Red Cross Plasma Derivatives Laboratory (Procedure for Factor IX Coagulation Assay, March 1992). Briefly, each well of a plastic Coag-a-mate tray received 90 µl of Factor IX-deficient plasma plus 10 µl of a Factor IX standard or sample, diluted with Tris/saline/BSA. The tray was then placed on an automated analyzer (APTT mode, 240 second activation). The run is started, which automatically performed the addition of 100 µl of APTT reagent and 100 µl of 0.025 M $CaCl_2$. Data obtained using a standard Factor IX preparation are fitted to the equation y=ax+b where y=clotting time and x=Factor IX, which is then used to determine the amount of Factor IX in a sample. Standards of normal plasma reference pool (Sigma) and human Factor IX derived from plasma are used in the assay. Duplicates of purified recombinant human Factor IX, human Factor IX, and normal plasma reference pool samples are run at each dilution. The rhFIX in the 5 mM $Ca^{2+}$ a specific activity of about 150-250 u/mg. The rhFIX in the 10 mM $Ca^{2+}$ a specific activity of about 100 u/mg or less. The FIX in the 15 mM $Ca^{2+}$ a specific activity of less than about 50 u/mg. The rhFIX in the 2 M NaCl gives a specific activity of less than 25 u/mg. The specific activity of the rhFIX of normal plasma reference pool is defined as 250 u/mg where the overall activity of the pool is 1 u/ml while containing 4 ug/ml of rhFIX.

Example 16

A milk derivative containing recombinant Human Factor IX processed from milk of transgenic pigs containing Long WAP-FIX-cDNA having high level expression of rhFIX achieved without using "gene rescue" from a milk protein gene.

A milk derivative concentrate of recombinant Human FIX useful for oral delivery of rhFIX is made from the milk of a transgenic pig containing a transgene composed of the 2.5 kbp mouse whey acidic protein promoter (WAP), the cDNA encoding human FIX, and a 1.6 kbp fragment of the 3' UTR of WAP. The expression level is about 0.1-0.5 g/l of rhFIX. Greater than about 80% of the rhFIX is biologically active. The skim milk is treated with a chelating agent such as 100 mM EDTA pH 7.5 or 100 mM Sodium Citrate pH 6.5 to clarify the milk of casein micelles. The clarified whey is passed over a DEAE-Sepharose or DEAE-Cellulose chromatographic column and the rhFIX is adsorbed. This adsorbed rhFIX is selectively desorbed from the anion exchange column using 5 mM $Ca^{2+}$ Tris-buffered-saline 150 mM NaCl (TBS). This eluted fraction of rhFIX containing selected, highly biologically active fractions of rhFIX is useful for oral delivery of rhFIX for therapeutic treatment of hemophilia B patients is pass through a 0.2 micron filter top remove bacterial contamination and then lyophilized to a powder. The rhFIX in the DEAE-column eluate has a composition that is volume reduced and concentrated by 25 to 50-fold over that of starting skim milk.

Example 17

A therapeutic application achieving oral delivery of the recombinant Human Factor IX using a milk derivative made from the milk of transgenic pigs containing Long WAP-FIX-cDNA having high level expression of rhFIX achieved without using "gene rescue" from a milk protein gene.

The lyophilized powder of example 5 is reconstituted with aqueous containing ordinary bovine milk cream such as to restore the volume to 25 to 50-fold concentrate over that of the original whey. The mixture is fed to hemophilia type B mice shortly after their first meal post sleep where less than 1 ml is fed to each mouse. The bleeding time by measured tail incision is measured 12 hours later. The corrected bleeding time is 5-7 minutes as compared to 11 minutes for a control hemophiliac mouse who was not fed the rhFIX milk concentrate and 5 minutes for a normal mouse with normal hemostasis.

Example 18

A therapeutic application achieving oral immunotolerization of recombinant Human Factor IX derived from Chinese Hamster Ovary cells using a milk derivative containing recombinant FIX made from milk of transgenic pigs containing Long WAP-FIX-cDNA having high level expression of rhFIX achieved without using "gene rescue" from a milk protein gene.

Mice are fed the reconstituted mixture from example 16 for everyday consecutively for one month and after this month, they are sensitized with complete Freund's adjuvant and recombinant human Factor IX. After 12 days, blood samples from these mice do not respond with the presence of anti-human FIX antibodies and also does not respond with T-cells which are activated by the presence of recombinant FIX derived from Chinese Hamster ovary cells. Control mice that have not been fed the mixture from example 16 are sensitized with the same adjuvant and human FIX mixture. After 12-14 days the blood of these human FIX sensitized control mice exhibit a strong immunological response consisting of both anti-human FIX antibodies and T-cells that are activated by the presence of human FIX.

Example 19

A therapeutic application achieving oral immunotolerization of recombinant Human Factor IX derived from cell culture by using a milk derivative containing recombinant FIX made from milk of transgenic pigs containing Long WAP-FIX-cDNA having high level expression of FIX achieved without using "gene rescue" from a milk gene.

Mice are fed the reconstituted mixture from example 16 for everyday consecutively for one month and after this month, they are sensitized with complete Freund's adjuvant and recombinant human Factor IX derived from Chinese Hamster Ovary cells. After 12 days, blood samples from these mice do not respond with the presence of anti-human FIX antibodies and also does not respond with T-cells which are activated by the presence of recombinant FIX derived from the milk of transgenic pigs. Control mice that have not been fed the mixture from example 16 are sensitized with the same adjuvant and rhFIX mixture. After 12-14 days the blood of these human FIX sensitized control mice exhibit a strong immunological response consisting of both anti-human FIX antibodies and T-cells that are activated by the presence of rhFIX.

Example 20

A therapeutic application achieving oral immunotolerization of Human Factor IX derived from plasma by using a milk derivative containing recombinant FIX made from milk of transgenic pigs containing Long WAP-FIX-cDNA having high level expression of rhFIX achieved without using "gene rescue" from a milk protein gene.

Mice are fed the reconstituted mixture from example 16 everyday consecutively for one month and after this month, they are sensitized with complete Freund's adjuvant and recombinant human Factor IX. After 12 days, blood samples from these mice do not respond with the presence of anti-human FIX antibodies and also does not respond with T-cells which are activated by the presence of recombinant or human FIX. Control mice that have not been fed the mixture from example 16 are sensitized with the same adjuvant and human FIX mixture. After 12-14 days the blood of these human FIX sensitized control mice exhibit a strong immunological response consisting of both anti-human FIX antibodies and T-cells that are activated by the presence of human FIX derived from plasma.

What is claimed is:

1. A milk derivative concentrate of recombinant human FIX useful for oral delivery to a patient comprising a biologically active Factor IX derived from milk produced by a transgenic pig whose genome comprises a stably integrated exogenous DNA molecule encoding human Factor IX, wherein said human Factor IX was purified and concentrated over the Factor IX present in said milk of said transgenic pig, and mixed with a pharmaceutically acceptable carrier to form said milk derivative concentrate comprising a dose for oral delivery from 2.5 mg/ml to 250 mg/ml of Factor IX.

2. The milk derivative concentrate according to claim 1, wherein said purified human Factor IX was lyophilized to a powder prior to mixing with said carrier.

3. The milk derivative concentrate according to claim 1, wherein said carrier is milk or a milk derivative.

4. The milk derivative concentrate according to claim 1, wherein said human Factor IX was purified via chromatography.

5. The milk derivative concentrate according to claim 1, wherein said human Factor IX comprises a specific activity of about 150-250 U/mg in 5 mM $Ca^{2+}$.

6. A method of treating a patient having hemophilia B comprising orally administering to said patient a hemophilia B symptom preventing or ameliorating amount of a milk derivative concentrate of recombinant human FIX comprising a biologically active Factor IX derived from milk produced by a transgenic pig whose genome comprises a stably integrated exogenous DNA molecule encoding human Factor IX, wherein said human Factor IX was purified and concentrated over the Factor IX present in said milk of said transgenic pig, and mixed with a pharmaceutically acceptable carrier to form said milk derivative concentrate, wherein said amount of orally administered Factor IX comprises from 2.5 mg/ml to 250 mg/ml of Factor IX, and results in reduced bleeding time in said patient as compared to no administration of Factor IX to said patient, achieving a therapeutic effect in treating hemophilia B and achieving oral immunotolerization of said Factor IX.

7. The method according to claim 6, wherein said purified human Factor IX was lyophilized to a powder prior to mixing with said carrier.

8. The method according to claim 6, wherein said carrier is milk or a milk derivative.

9. The method according to claim 6, wherein said human Factor IX was purified via chromatography.

10. The method according to claim 6, wherein said human Factor IX comprises a specific activity of about 150-250 U/mg in 5 mM $Ca^{2+}$.

11. The method according to claim 6, wherein said oral immunotolerization prevents the production of anti-Factor IX antibodies in said patient.

12. A method of treating a patient having hemophilia B comprising orally administering to said patient a hemophilia B symptom preventing or ameliorating amount of a milk derivative concentrate of recombinant human FIX consisting essentially of a biologically active Factor IX derived from milk produced by a transgenic pig whose genome comprises a stably integrated exogenous DNA molecule encoding human Factor IX, wherein said human Factor IX was purified and concentrated over the Factor IX present in said milk of said transgenic pig, and mixed with a pharmaceutically acceptable carrier to form said milk derivative concentrate, wherein said amount of orally administered Factor IX comprises from 2.5 mg/ml to 250 mg/ml of Factor IX, and results in reduced bleeding time in said patient as compared to no administration of Factor IX to said patient, achieving a therapeutic effect in treating hemophilia B and achieving oral immunotolerization of said Factor IX.

13. The method according to claim 12, wherein said purified human Factor IX was lyophilized to a powder prior to mixing with said carrier.

14. The method according to claim 12, wherein said carrier is milk or a milk derivative.

15. The method according to claim 12, wherein said human Factor IX was purified via chromatography.

16. The method according to claim 12, wherein said human Factor IX comprises a specific activity of about 150-250 U/mg in 5 mM $Ca^{2+}$.

17. The method according to claim 12, wherein said oral immunotolerization prevents the production of anti-Factor IX antibodies in said patient.

18. The milk derivative concentrate according to claim 1, wherein said human Factor IX was purified and concentrated by 25 to 50 fold over the Factor IX present in said milk of said transgenic pig.

19. The method according to claim 6, wherein said human Factor IX was purified and concentrated by 25 to 50 fold over the Factor IX present in said milk of said transgenic pig.

20. The method according to claim 12, wherein said human Factor IX was purified and concentrated by 25 to 50 fold over the Factor IX present in said milk of said transgenic pig.

\* \* \* \* \*